United States Patent [19]

Dyson et al.

[11] Patent Number: 5,231,181
[45] Date of Patent: Jul. 27, 1993

[54] PROCESS FOR THE PREPARATION OF (8AS,12AS,13AS)-DECAHYDROISOQUINO ((2,1-G) (1,6)-NAPHTHYRIDIN-8-ONE DERIVATIVES

[75] Inventors: Norman H. Dyson, Palo Alto; John O. Gardner, Los Altos; John C. Rohloff, San Mateo, all of Calif.

[73] Assignee: Syntex (U.S.A.) Inc., Palo Alto, Calif.

[21] Appl. No.: 673,693

[22] Filed: Mar. 21, 1991

[51] Int. Cl.[5] .......................................... C07D 455/03
[52] U.S. Cl. ...................................... 546/48; 546/70; 562/401; 562/402
[58] Field of Search ................. 562/401, 402; 546/48, 546/70

[56] References Cited

U.S. PATENT DOCUMENTS

| | | | |
|---|---|---|---|
| 4,791,108 | 12/1988 | Clark | 514/233.2 |
| 4,886,798 | 12/1989 | Clark | 514/233.2 |
| 4,956,365 | 9/1990 | Clark et al. | 514/233.2 |
| 4,960,891 | 10/1990 | Clark et al. | 514/233.2 |
| 5,049,668 | 9/1991 | Wall et al. | 546/48 |

OTHER PUBLICATIONS

Investigation on the Chemistry of Berbans, by Szabo et al., Nouv. J. Chimie, 4(3), 199-202 (1980).
New Annelation Reaction of Cyclic Schiff Bases, by Akhrem et al., Synthesis, (12) 996 (1980).

*Primary Examiner*—Marianne M. Cintins
*Assistant Examiner*—Catherine S. Scalzo
*Attorney, Agent, or Firm*—Brian Lewis; David A. Lowin; Tom M. Moran

[57] ABSTRACT

The invention provides a process for preparing single enantiomers of compounds represented by the formula:

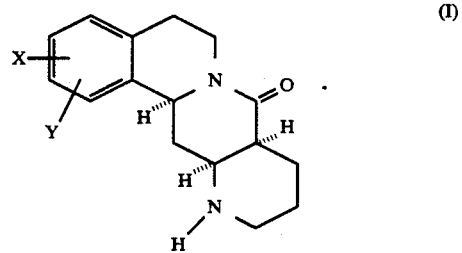

(I)

and chiral acid addition salts thereof; wherein:
X and Y are independently hydrogen; lower alkyl; lower alkoxy; or halo; or X and Y taken together is methylenedioxy or ethylene-1,2-dioxy;
which includes reduction of a compound represented by the formula:

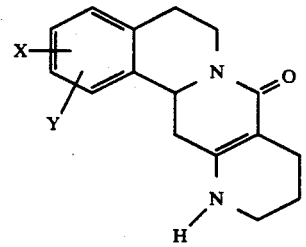

to give a mixture of stereoisomers represented by the formula:

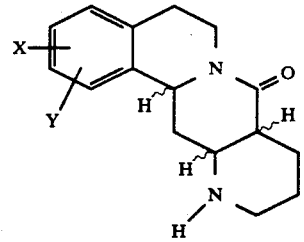

wherein each wavy line independently represents a bond in either the α or β position;
followed by dissolving the mixture of stereoisomers and a chiral resolving acid in a suitable solvent and allowing the solution to crystallize, giving a salt of the desired enantiomer.

22 Claims, No Drawings

PROCESS FOR THE PREPARATION OF (8AS,12AS,13AS)-DECAHYDROISOQUINO ((2,1-G) (1,6)-NAPHTHYRIDIN-8-ONE DERIVATIVES

BACKGROUND OF THE INVENTION

1. Field of the Invention

The invention relates to a process, and the intermediates useful in such a process, for the preparation of decahydroisoquino[2,1-g][1,6]naphthyridin-8-one derivatives as single enantiomers, and chiral acid addition salts thereof. The invention also relates to the use of such derivatives for a preferred preparation of decahydro-8H-isoquino[2,1-g][1,6]naphthyridine compounds as single enantiomers, examples of which are disclosed in U.S. Pat. Nos. 4,791,108, 4,886,798 and 4,956,365. The exemplified decahydro-8H-isoquino[2,1-g][1,6]naphthyridine compounds exhibit selective $\alpha_2$-blockade in mammals, and are therefore useful as medicaments for the treatment of physiological conditions affected by such selective blockade.

2. Previous Disclosures

Processes for the preparation of compounds of formula (I), as single enantiomers or as a mixture of enantiomers, are disclosed in U.S. patent application Ser. No. 336,993, and in U.S. Pat. Nos. 4,791,108, 4,886,798 and 4,956,365, the disclosures of which are hereby incorporated by reference.

The present process provides for an improved preparation of single enantiomers represented by the formula (I), i.e. the (8aS,12aS,13aS) enantiomer, and chiral acid addition salts thereof represented by the formula (IA) (as shown in the Summary of the Invention). The invention provides most particularly a process for the large-scale production of (I) and (IA). The process has surprising advantages over previously disclosed processes in that it does not require the use of low temperatures (some steps of previous processes were carried out at $-78°$ C.), does not require expensive nicotinic acid derivatives as starting materials, requires no unwieldy and time-consuming chromatographic separations, does not require isolation of intermediates at each step (and those intermediates that are separated are highly crystalline, thus simplifying the separation procedure), and the hydrogenation step may be adapted to be carried out at either high or low pressure. In addition, the resolution step surprisingly provides for a highly efficient separation of a single enantiomer from a mixture of diastereoisomers, in contrast to conventional procedures that require multiple crystallizations to separate the isomers from a single racemic compound.

SUMMARY OF THE INVENTION

In a first aspect the present invention provides a process for the preparation of single enantiomers represented by the formula (IA):

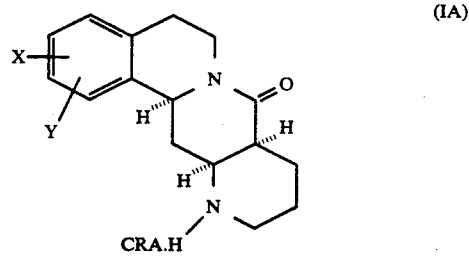

wherein:

X and Y are independently hydrogen; lower alkyl of one to six carbon atoms; lower alkoxy of one to six carbon atoms; or halo; or X and Y when adjacent and taken together are methylenedioxy or ethylene-1,2-dioxy; and CRA is a chiral resolving acid; and includes the step of dissolving a mixture of stereoisomers represented by the formula:

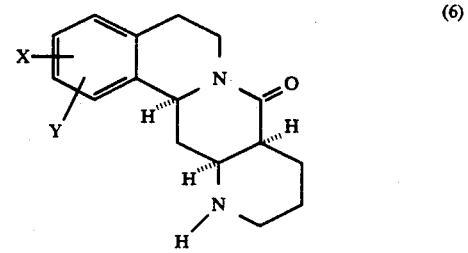

wherein each wavy line independently represents a bond in either the $\alpha$ or $\beta$ position;

together with a chiral resolving acid in a suitable solvent; and allowing the solution to crystallize. The preferred CRA is d-10-camphorsulfonic acid.

A second aspect of the invention relates to the process for the preparation of those enantiomers of formulae (I) and (IA) in which X is 3-methoxy and Y is hydrogen, or X and Y taken together is 2,3-methylenedioxy.

A third aspect of the invention relates to the process for the conversion of compounds of formula (IA) to compounds of the formula:

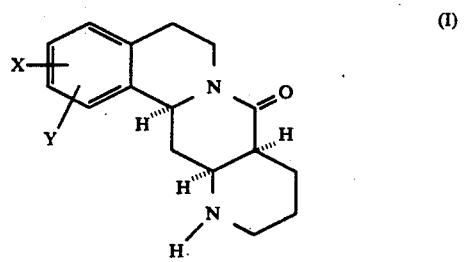

by treatment with a base.

A fourth aspect of the invention relates to the process for the conversion of compounds of formula (I) or (IA) to compounds of the formula

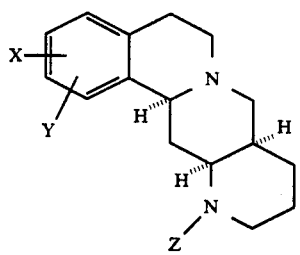

(II)

wherein X and Y are as defined above and Z is —SO$_2$R or —C(O)NR$^3$R$^4$, in which;

R is lower alkyl of one to six carbon atoms; phenyl optionally substituted by one or two substituents chosen from halo, amino, lower alkyl of one to four carbon atoms and lower alkoxy groups of one to four carbon atoms; —(CH$_2$)$_m$OR$^1$; or —NR$^1$R$^2$; wherein:

m is an integer of 1 to 6 and R$^1$ and R$^2$ are independently lower alkyl; or R$^1$ and R$^2$ taken together with the nitrogen to which they are attached or R$^3$ and R$^4$ taken together with the nitrogen to which they are attached represent a heterocycle of the formula:

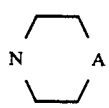

wherein A is —CH$_2$—, —NR$^1$—or oxygen; or R$^3$ and R$^4$ are independently alkyl of 1-8 carbon atoms; phenyl; or phenyl lower alkyl; in which any phenyl group may be optionally substituted by one or two substituents chosen from halo, lower alkyl of one to four carbon atoms and lower alkoxy of one to four carbon atoms;

by (a) contacting a compound of the formulae (I) or (IA) with a compound of the formula ZV, where Z is as defined above but R$^3$ and R$^4$ are not hydrogen, and V is a leaving group, preferably bromo or chloro, to give a compound of the formula:

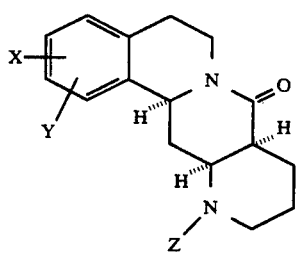

(7)

followed by:

(b) reducing the compound of formula (7) to give the compound of formula (II).

A fifth aspect of the invention relates to the process for the preparation of the mixture of stereoisomers represented as formula (6), where X and Y are as defined above, and includes the following reaction steps:

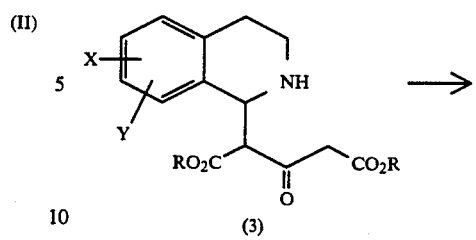

where R is lower alkyl

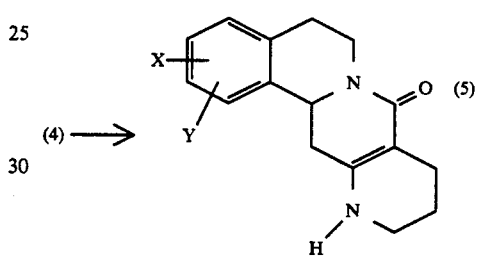

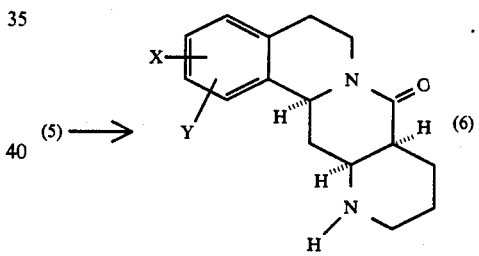

wherein each wavy line independently represents a bond in either the α or β position;

A sixth aspect of the invention relates to the novel intermediates of formula (5).

DETAILED DESCRIPTION OF THE INVENTION

Definitions

As used herein:

"Alkyl" means a branched or unbranched saturated hydrocarbon chain containing 1 to 8 carbon atoms, such as methyl, ethyl, propyl, tert-butyl, n-hexyl, n-octyl and the like.

"Lower alkyl" means a branched or unbranched saturated hydrocarbon chain containing 1 to 6 carbon atoms, such as methyl, ethyl, propyl, isopropyl, tert-butyl, butyl, n-hexyl and the like, unless otherwise indicated; for example, phenyl optionally substituted by lower alkyl groups of one to four carbon atoms.

"Lower alkoxy" means the group —O—(lower alkyl) wherein lower alkyl is as herein defined.

"Cycloalkyl" as used herein means a saturated monovalent monocyclic hydrocarbon radical containing 3-8 carbon atoms, such as cyclopropyl, cyclobutyl, cyclopentyl, cyclohexyl, cycloheptyl and cyclooctyl.

"Halo" means fluoro, chloro, bromo and iodo.

"Phenyl" as used herein encompasses all possible isomeric phenyl radicals optionally monosubstituted or disubstituted with a substituent selected from the group consisting of lower alkyl, lower alkoxy, —NH₂, hydroxy, trifluoromethyl and halo.

"Phenyl lower alkyl" as used herein denotes phenyl as defined above attached to a lower alkyl group as defined above.

The term "leaving group" means a group capable of being displaced by a nucleophile in a chemical reaction.

The terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform ("CHCl₃"), methylene chloride (or dichloromethane or "CH₂Cl₂"), diethyl ether, ethyl acetate, acetone, methylethyl ketone, methanol, ethanol, propanol, isopropanol, tert-butanol, dioxane, pyridine, and the like]. Unless specified to the contrary, the solvents used in the reactions of the present invention are inert solvents.

The term "chiral acid" or "chiral resolving acid" or "CRA" refers to those chiral acids that react with the enantiomer (I) to form crystalline diastereomeric salts represented as formula (IA). Exemplary of such chiral acids are the optically active forms of 10-camphorsulfonic acid, 2-bromo-10-camphorsulfonic acid, camphoric acid, menthoxyacetic acid, tartaric acid, malic acid, mandelic acid, diacetyltartaric acid, N-acetyl-L-leucine, quinic acid, 2,3,4,6-di-O-isopropylidene-2-keto-L-gulonic acid, pyrrolidine-5-carboxylic acid, and the like. While at present the only chiral resolving acid found to conform to the foregoing requirements is d-10-camphorsulfonic acid, it is contemplated that other suitable chiral acids may be successfully employed upon optimization of the reaction conditions and environment. Thus the preferred chiral resolving acid is d-10-camphorsulfonic acid.

The term "suitable solvent" refers to those solvents of Reaction Scheme III, Step 5, that dissolve the mixture of stereoisomers represented as formula (6) together with a chiral resolving acid as defined above, and from which solution a single enantiomer of formula (IA) crystallizes. Exemplary of such solvents are ketones (preferably acetone), alcohols (preferably isopropanol), and ethers (preferably dioxane), and combinations of two or more of such solvents.

"Strong base" as used herein denotes an inorganic base such as sodium hydroxide, potassium hydroxide, sodium carbonate, potassium carbonate, and the like.

"Strong acid" denotes an inorganic acid such as hydrochloric acid, sulfuric acid, nitric acid, and the like.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl.

The terms "α" and "β" indicate the specific stereochemical configuration of a substituent at an asymmetric carbon atom in a chemical structure as drawn. Thus "α", denoted by a broken line, indicates that the group at the position in question is below the general plane of the molecule as drawn, and "β", denoted by a bold line, indicates that the group at the position in question is above the general plane of the molecule as drawn.

The absolute stereochemistry at carbons 8a, 12a and 13a is specified according to the Cahn-Ingold-Prelog R-S system. When the compound is a pure enantiomer the stereochemistry at each chiral carbon may be specified by either R or S. When a compound is a racemic mixture the stereochemistry at each chiral carbon may be specified by either RS or SR by reference to a single enantiomer of the racemate. In this manner relative stereochemistry is conveyed unambiguously.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate. Unless otherwise indicated the mixture of compounds represented by formula (6) is intended to depict both racemic and non-racemic mixtures of enantiomers.

"Diastereoisomers" are stereoisomers which are not mirror-images of each other.

The compounds of formulae (I), (IA), (5) and (6) will be named using the numbering system shown below.

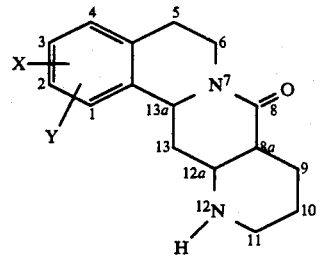

Following are examples of how representative compounds are named:

The compound of formula (I) as a racemic mixture wherein X is 3-methoxy and Y is hydrogen is named:
(±)-3-methoxy-5,6,8aβ,9,10,11,12,12aβ,13,13aβ-decahydroisoquino[2,1-g][1,6]naphthyridin-8-one.

The single enantiomer of formula (I) wherein X is 3-methoxy and Y is hydrogen is named:
(8aS,12aS,13aS)-3-methoxy-5,6,8a,9,10,11,12,12a,13,13a-decahydro-8H-isoquino[2,1-g][1,6]naphthyridin-8-one.

A racemic compound of formula (5) wherein X is 3-methoxy and Y is hydrogen is named:
(±)-3-methoxy-5,6,9,10,11,12,13,13a-octahydroisoquino[2,1-g][1,6]naphthyridin-8-one.

The compounds of formula (4) will be named using the numbering system shown below.

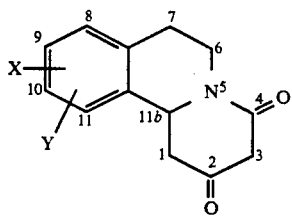

Following are examples of how representative compounds are named:

A compound of formula (4) wherein X is 3-methoxy and Y is hydrogen is named:
4-dioxo-9-methoxy-1,2,3,4,6,7-hexahydro-11bH-benzo[a]quinolizine.

The compounds of formula (I) or (IA) obtained by the present process are useful for the preparation of decahydro-8H-isoquino[2,1-g][1,6]naphthyridine derivatives, in particular those derivatives substituted at the 12-position. For example, compounds of the formula:

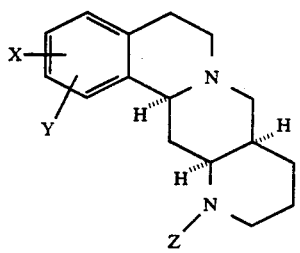

(II)

wherein X and Y are as defined above and Z is —SO$_2$R or —C(O)NR$^3$R$^4$, in which;

R is lower alkyl of one to six carbon atoms; phenyl optionally substituted by one or two substituents chosen from halo, amino, lower alkyl of one to four carbon atoms and lower alkoxy groups of one to four carbon atoms; —(CH$_2$)$_m$OR$^1$; or —NR$^1$R$^2$; wherein:

m is an integer of 1 to 6 and R$^1$ and R$^2$ are independently lower alkyl; or R$^1$ and R$^2$ taken together with the nitrogen to which they are attached or R$^3$ and R$^4$ taken together with the nitrogen to which they are attached represent a heterocycle of the formula:

wherein A is —CH$_2$—, —NR$^1$—or oxygen; or

R$^3$ and R$^4$ are independently alkyl of 1-8 carbon atoms; phenyl; or phenyl lower alkyl; in which any phenyl group may be optionally substituted by one or two substituents chosen from halo, lower alkyl of one to four carbon atoms and lower alkoxy of one to four carbon atoms.

The compounds of formula (II) are useful for the treatment of disease states which include, but are not limited to, depression, anxiety, excessive platelet aggregation, diabetes, elevated intraocular pressure, male impotence, irritable bowel syndrome, peripheral vascular disease, hypertension, obesity, shortened recovery from anesthesia and cyclic mood disturbances in females.

Processes whereby the compounds of formula (I) of the present invention are converted to the compounds of formula (II) are disclosed in U.S. patent application Ser. No. 336,993, and U.S. Pat. Nos. 4,791,108, 4,886,798 and 4,956,365, the relevant portions of which are hereby incorporated by reference.

PREFERRED EMBODIMENTS

Among the family of compounds prepared by the instant process, a preferred compound is that wherein X is 3-methoxy and Y is hydrogen. For the preparation of this compound the preferred chiral resolving acid is d-10-camphorsulfonic acid, which is preferably present in a molar ratio of about 1:1 in relation to the single enantiomer to be separated, and the preferred solvent is acetone. The crystallization is preferably carried out a temperature of about 20°–25° C., preferably for at least 12 hours.

A second preferred compound is that wherein X and Y taken together are 2,3-methylenedioxy. For this compound the preferred chiral resolving acid is d-10-camphorsulfonic acid, which is preferably present in a molar ratio of about 1:1 in relation to the single enantiomer to be separated, and the preferred solvent is dioxane. The crystallization is preferably carried out a temperature of about 20°–25° C., preferably for at least 12 hours.

The preferred method of reducing the compound of formula (5) is by catalyst and hydrogen, most preferably rhodium on alumina or platinum on alumina at a pressure of about 2–5 pounds per square inch in acetic acid.

Preparation of Starting Materials

The starting compounds represented by the formula (2), optionally substituted dihydroisoquinolines, may be prepared according to the method of Bischler-Napieralski, disclosed in Organic Reactions, Vol. VI, p 74 (1951), which is hereby incorporated by reference. This preparation starts with the cyclization of formamides of commercially-available optionally substituted phenylethylamines, as illustrated in Reaction Scheme I.

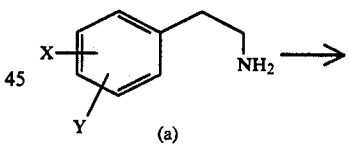

(a)

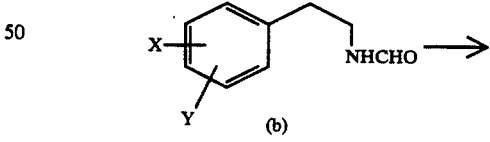

(b)

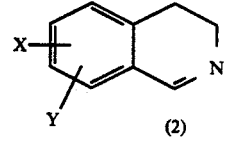

(2)

The compound of formula (a) is reacted with about 1–5 molar equivalents, preferably about 2 molar equivalents, of an alkyl formate, preferably ethyl formate. The reaction is carried out in an inert solvent, preferably toluene, at a temperature of about 50° C. up to the reflux temperature of the alkyl formate, preferably at reflux temperature, for about 1–24 hours, preferably about 6 hours. The product of formula (b) is isolated and purified by conventional means, preferably vacuum distillation.

The compound of formula (b) is then reacted with about 1-2 molar equivalents, preferably about 1.1 molar equivalents, of a dehydrating agent, preferably phosphorus pentachloride. The reaction is carried out in an inert solvent, preferably dichloromethane, at a temperature of about 25° C. up to reflux temperature, preferably at reflux temperature, for about 1-4 hours, preferably about 2 hours. The product of formula (2) is isolated and purified by conventional means.

Preparation of Compounds of Formula (6)

Reaction Scheme II shows the preparation of the mixture of stereoisomers represented as formula (6).

REACTION SCHEME II

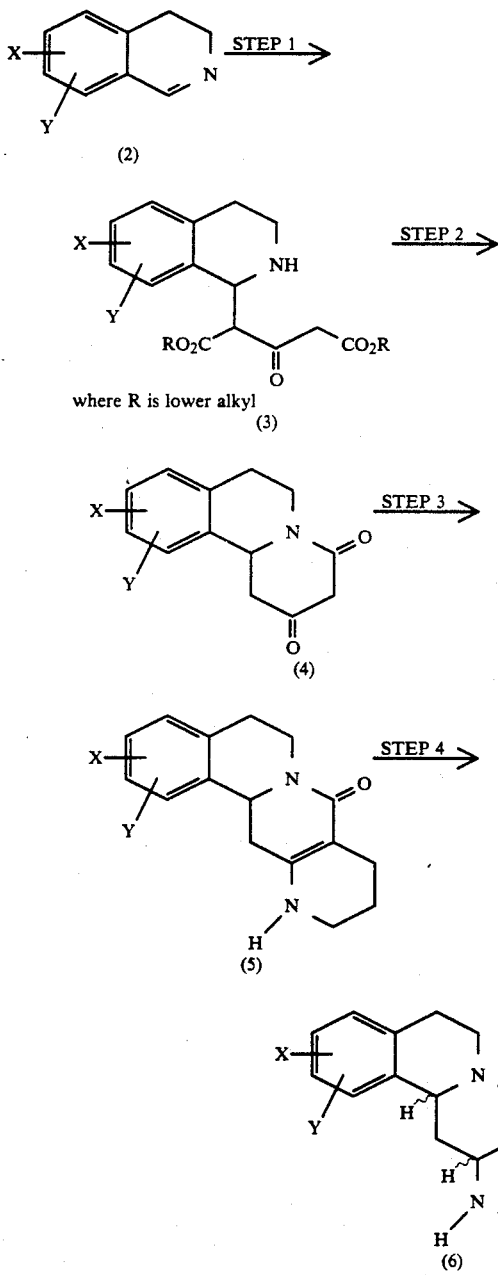

where R is lower alkyl

Step 1—Preparation of a compound of Formula (3)

The reaction of Step 1 in its broadest aspect comprises the reaction of a compound of the formula (2) with a compound of the formula $RO_2CCH_2C(O)CH_2CO_2R$ (a dialkyl 1,3-acetonedicarboxylate), where R is lower alkyl, preferably methyl. The dialkyl 1,3-acetonedicarboxylates are commercially available from, inter alia, Aldrich Chemical Co.

Typically, to a mixture of a compound of formula (2) and a protic solvent (such as water, ethanol, n-propanol or isopropanol, preferably water), about 1-2 molar equivalents, preferably about 1.1 molar equivalents, of an appropriate dialkyl 1,3-acetonedicarboxylate, preferably dimethyl 1,3-acetonedicarboxylate, is added at about 20°-25° C., and the mixture heated to about 40°-80° C., preferably about 55°-65° C. This temperature is maintained for about 10 minutes, and then the reaction mixture cooled to about room temperature. If the preferred solvent (water) is employed in Step 1, the resulting reaction mixture is washed with an inert solvent, preferably methylene chloride, and the next step (i.e. Step 2) is then carried out directly on the aqueous suspension of a compound of formula (3) thus obtained, thus avoiding the need for isolation of (3).

If the reaction is carried out in a non-aqueous solvent (preferably isopropanol), a 1-(1,3-alkoxy-carbonyl-2-oxopropan-1-yl)-1,2,3,4-tetrahydroisoquinoline derivative, a compound of formula (3), is isolated by conventional means, preferably filtration, and used as such in Step 2.

Step 2—Preparation of a compound of Formula (4)

The reaction of Step 2 in its broadest aspect comprises the reaction of a compound of formula (3) with a base to give a product that on acidification gives the compound of formula (4).

Typically a compound of formula (3) is suspended in a protic solvent, preferably water, at a temperature of about 20°-50° C., preferably about 25° C. About 3-12 molar equivalents, preferably about 4 molar equivalents, of a strong base (for example potassium hydroxide or sodium hydroxide, preferably sodium hydroxide) dissolved in water is added. The reaction mixture is maintained at a temperature of about room temperature, for about 12-48 hours, preferably about 24 hours. The reaction mixture is then acidified with a strong acid, preferably hydrochloric acid, to a pH of less than 3, keeping the temperature at about 10°-25° C., preferably about 25°-20° C., over a period of about 1 hour, and then maintaining the temperature at about 60° C., preferably about 40°-50° C., for about 10-24 hours, preferably about 18 hours, maintaining the pH at less than 3 by the addition of more acid as necessary over the course of the reaction. A 2,4-dioxo-1,2,3,4,6,7-hexahydro-11bH-benzo[a]quinolizine derivative, a compound of formula (4), is isolated by conventional means, preferably filtration.

Step 3—Preparation of a compound of Formula (5)

The reaction of Step 3 in its broadest aspect comprises the reaction of a compound of the formula (4) with a 3-halopropylamine of the formula $W(CH_2)_3NH_2 \cdot HW$, where W is chloro or bromo, preferably bromo (for example 3-bromopropylamine hydrobromide, commercially available from, inter alia, Aldrich Chemical Co.), in the presence of a base to give the compound of formula (5).

Typically a compound of formula (4) is dissolved in an appropriate solvent, such as isopropanol, chlorobenzene, 1,1,1-trichloroethane, toluene, or preferably n-butanol, and about 1-2 molar equivalents, preferably about 1.1 molar equivalents, of the appropriate 3-halopropylamine added, preferably 3-bromopropylamine as its hydrobromide salt, followed by about 1.5 to 4 molar equivalents, preferably about 2.2 molar equivalents, of a tertiary base (such as triethylamine, collidine, N-methylmorpholine, N,N-dimethylaniline or 2,6-lutidine, preferably 2,6-lutidine). The mixture is heated to a temperature of about 80° C. to reflux temperature, preferably about reflux temperature, for about 20 minutes to 4 hours, preferably about 1 hour. A (±)-5,6,9,10,11,12,13,13a-octahydroisoquino[2,1-g][1,6]naphthyridin-8-one derivative, a compound of formula (5), is isolated by conventional means, and purified for example by crystallization from aqueous methanol.

Step 4—Preparation of the Mixture of Stereoisomers Represented as Formula (6)

The reaction of Step 4 in its broadest aspect comprises the reduction of a compound of the formula (5), with a suitable hydrogenation catalyst or by chemical reduction, in an inert solvent to give the mixture of stereoisomers represented as formula (6).

Typically a compound of formula (5) is dissolved in a protic solvent (such as ethanol, n-propanol, isopropanol, propionic acid, or acetic acid, preferably acetic acid) and then hydrogenated. The reduction may be accomplished using palladium hydroxide in ethanol/hydrochloric acid as a catalyst, or by carrying out a chemical reduction, using for example sodium cyanoborohydride, diborane, Wilkinson's catalyst, cationic rhodium complexes, and the like. Preferably the reduction is carried out using a suitable heterogeneous catalyst (for example platinum oxide, platinum oxide on carbon, platinum on carbon, rhodium on carbon, rhodium on alumina or platinum on alumina, most preferably rhodium on alumina or platinum on alumina).

For example, for every gram of a compound of formula (5) in a solution of acetic acid is added from 0.01 to 0.4 g, preferably about 0.05 g, of a suitable catalyst, preferably 5% rhodium on alumina catalyst or 5% platinum on alumina, and the mixture hydrogenated at a pressure of about atmospheric pressure to 80 psi, preferably about 2-5 psi. The reaction is conducted at a temperature of about 18° to 50° C., preferably about 20°-25° C., until the starting compound of formula (5) is no longer detected in the reaction mixture. Higher pressures result in shorter reaction times, as does increasing the quantity of catalyst used, but on a large scale lower pressures and a minimum quantity of catalyst are often preferred for reasons of convenience and economy. When the reaction is substantially complete, the mixture of stereoisomers represented as formula (6), a mixture of racemic decahydroisoquino[2,1-g][1,6]naphthyridin-8-one derivatives, is isolated by conventional means.

It should be understood that structure (6) as illustrated in Reaction Scheme II is intended to represent the mixture of stereoisomers obtained by reduction of the compound of formula (5). The mixture of stereoisomers (6), as prepared by the preferred method of reduction of the compound of formula (5), comprises a mixture of the single enantiomer of formula (I) as a racemic compound and at least one of the other possible racemic compounds that may be represented by formula (6).

That is, formula (6) represents a mixture of the racemic compound represented by the formula (6a):

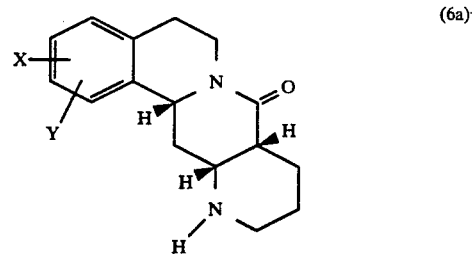

and at least one of the racemic compounds represented by the formulae (6b), (6c) and (6d):

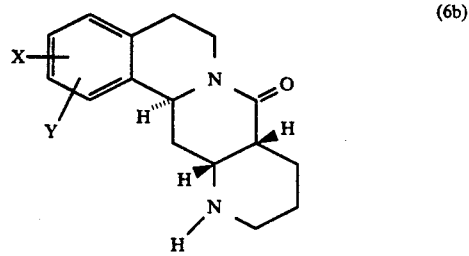

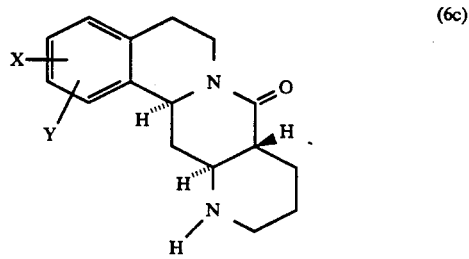

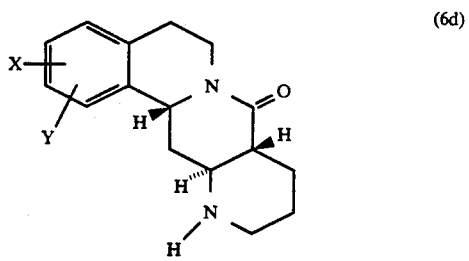

It is possible that all of the above stereoisomers may be obtained by reduction of the compound of formula (5), depending upon the catalyst, pressure and solvent chosen, and other relevant reaction conditions. However, under the preferred reduction conditions the mixture represented by (6) is believed to consist of a mixture of the racemic compounds (6a), (6b) and (6c).

It is possible that non-racemic mixtures of the stereoisomers represented by the formula (6) could be obtained, for example by asymmetric hydrogenation of racemic or non-racemic (5), or by conventional reduction of non-racemic (5), which could be obtained by standard resolution techniques. The instant process can be applied equally to racemic or non-racemic mixtures of stereoisomers which might be represented by the formula (6), with the proviso that the single enantiomer of formula (I) must be present in the mixture.

Preparation of the Compounds of Formulae (I) and (IA)

Reaction Scheme III illustrates the separation of the compound of formula (IA) from the mixture of stereoisomers of formula (6) and its conversion to the compound of formula (I).

REACTION SCHEME III

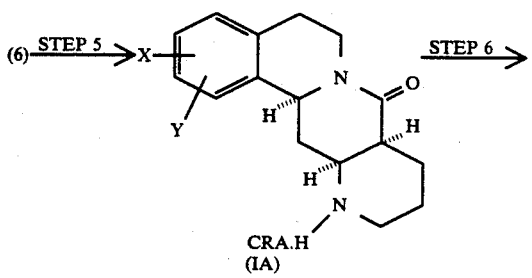

where CRA is a chiral resolving acid

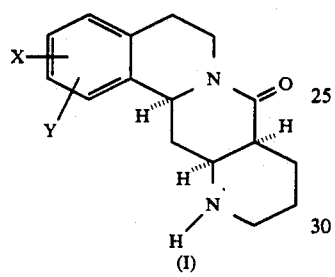

Step 5—Preparation of a compound of Formula (IA)

The reaction of Step 5 in its broadest aspect comprises the separation of a diastereoisomeric salt of formula (IA) from the mixture of stereoixomers represented as formula (6), first forming (IA) by reaction of (6) with a chiral acid and then selectively crystallizing the resultant diastereoisomeric salt of formula (IA) from solution.

Typically the mixture of stereoisomers of formula (6) is dissolved in an inert solvent, preferably a lower alkanol, a di(lower alkyl)ketone, dioxane, and the like, or mixtures thereof, most preferably acetone where X is 3-methoxy and Y is hydrogen, and most preferably dioxane where X and Y taken together are methylenedioxy. A suitable chiral resolving acid is then added, preferably in an amount about equimolar to that of the amount of the enantiomer of formula (I) present in the mixture of stereoisomers (6). That is, the molar ratio of the chiral resolving acid to the single enantiomer (I) to be separated is preferably between about 0.9:1 and 1.1:1, most preferably about 1:1. The amount of the desired enantiomer of formula (I) present in the mixture of stereoisomers (6) is generally between about 30% and 40%. Therefore the absolute amount of the chiral resolving acid used (as measured against the total amount of the stereoisomers of formula (6) present) is preferably about 0.3 to 0.4 molar equivalents, most preferably about 0.33 molar equivalents. While at present the only chiral resolving acid found to be suitable is d-10-camphorsulfonic acid, it is contemplated that other chiral acids may be successfully employed upon optimization of the reaction conditions and environment. Thus the preferred chiral resolving acid is d-10-camphorsulfonic acid. The solution is maintained at a temperature of about 0° to 50° C., preferably about 25° C., and allowed to crystallize for about 12–72 hours, preferably about 24 hours. When crystallization is substantially complete, a chiral acid salt of a (8aS,12aS,13aS)5,6,8a,9,10,11,12,-12a,13,13a-decahydroisoquino[2,1-g][1,6]naphthyridin-8-one derivative, a compound of formula (IA), is isolated in substantially pure form by filtration. If desired, the salt may be further purified by reflux with isopropanol, cooling and filtration.

Step 6—Preparation of a compound of Formula (I)

The reaction of Step 6 comprises treatment of a chiral acid salt of formula (IA) with a strong base (for example sodium hydroxide, potassium carbonate, and the like) or a tertiary organic base (such as triethylamine, collidine, N-methylmorpholine, N,N-dimethylaniline or 2,6-lutidine, preferably N-methylmorpholine), to give a (8aS,-12aS,13aS)-5,6,8a,9,10,11,12,12a,13,13a-decahydroisoquino[2,1-g][1,6]naphthyridin-8-one derivative, a single enantiomer of formula (I).

Preparation of the Compounds of Formula (II)

A preferred procedure for the conversion of compounds of formula (I) to (II) is set forth in pending U.S. patent application Ser. No. 336,993, and is shown below in Reaction Scheme IV.

REACTION SCHEME IV

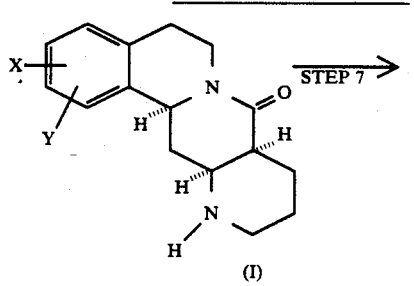

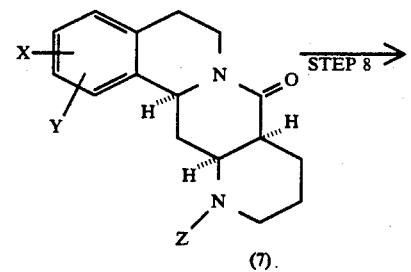

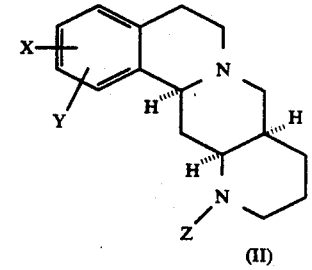

where X, Y and Z are as defined above.

This process, in contrast to other processes previously disclosed, affords an intermediate of formula (7) which is highly crystalline, and is thus easily isolated, purified and manipulated on a large scale.

Step 7—Preparation of a compound of Formula (7)

The reaction of Step 7 in its broadest aspect comprises the reaction of a compound of the formula (I) with a compound of the formula ZV, where Z is —$SO_2R$ or —$C(O)NR^3R^4$, in which R is as defined above, $R^3R^4$ are as defined above but are not hydrogen, and V is a leaving group, preferably halo, most preferably bromo or chloro. Where ZV is a substituted sulfonyl halide of the formula $VSO_2R$, V is preferably chlorine or bromine; where ZV is a compound of the formula $VC(O)NR^3R^4$, V is preferably chlorine. The sulfonyl halides of formula $VSO_2R$ are either commercially available from, inter alia, Aldrich Chemical Co., or may be prepared according to the method of Zeigler and Sprague, disclosed in J. Org. Chem., Vol 16, p 621 (1951). The carbamyl chlorides of formula $R^3R^4NC(O)Cl$ are either commercially available from, inter alia, Aldrich Chemical Co., or may be prepared by methods well known in the art.

Typically a compound of formula (I) is dissolved in an inert organic solvent, such as benzene, toluene, ethyl acetate, tetrahydrofuran, diethyl ether, chloroform or preferably dichloromethane, containing from 1–10 molar equivalents, preferably about 2 molar equivalents, of an inorganic base such as sodium carbonate, potassium bicarbonate or the like, or preferably a tertiary organic base, (for example triethylamine, pyridine, N-methylmorpholine, N-methylpiperidine and the like, preferably N-methylmorpholine). The mixture is cooled to about $-10°$ to $10°$ C., preferably about $0°$ C., and about 1–4 equivalents, preferably about 1.5 molar equivalents, of an appropriately substituted sulfonyl halide of formula $VSO_2R$ added and the mixture stirred for about 10 minutes to 2 hours, preferably about 30 minutes at a temperature of about $10°$ to $40°$ C., preferably about $25°$ C. When the reaction is substantially complete, a (8aS,-12aS,13aS)-12-methanesulfonyl-5,6,8a,9,10,11,12,-12a,13,13a-decahydroisoquino[2,1-g][1,6]naphthyridin-8-one derivative, a compound of formula (7) where Z is —$SO_2R$, is isolated by conventional means, and purified, if desired, by crystallization from an inert solvent.

Alternatively, the mixture of a compound of formula (I) and base as above, preferably triethylamine, is cooled to about $0°$ to $40°$ C., preferably about $25°$ C., and about 1–4 molar equivalents, preferably about 1.1 molar equivalents, of an appropriately substituted compound of formula $R^3R^4NC(O)Cl$ added and the mixture stirred for about 5–30 hours, preferably about 16 hours. When the reaction is substantially complete, a (8aS,-12aS,13aS)-12-N,N-dialkylaminocarbonyl-5,6,8a,9,10,11,12,12a,13,13a-decahydroisoquino[2,1-g][1,6]naphthyridin-8-one derivative, a compound of formula (7) where Z is —$C(O)NR^3R^4$, is isolated as above.

Alternatively, a compound of formula (7) where Z is —$C(O)NR^3R^4$, where $R^3$ is hydrogen and $R^4$ is other than hydrogen, may be prepared by reacting a compound of formula (I) with an isocyanate of the formula $R^4NCO$. Typically, the compound of formula (2) is dissolved in an inert solvent as defined above, preferably toluene, and reacted with from 1 to 1.5 molar equivalents, preferably about 1.0 molar equivalents, of the compound of formula $R^4NCO$. The reaction is carried out at a temperature of about $0°–40°$ C., preferably about $25°$, for about 5–30 hours, preferably about 16 hours. When the reaction is substantially complete, a compound of formula (7) where Z is —$C(O)NHR^4$, is isolated as above.

A compound of formula (7) where Z is —$C(O)NH_2$ is prepared by reacting a compound of formula (I) with potassium isocyanate in the presence of an acid, preferably acetic acid.

Alternatively, a compound of formula (7) where Z is —$C(O)NR^3R^4$ may be prepared by first reacting a compound of formula (I) with phosgene, then reacting the resultant carbamoyl chloride with an amine of formula $HNR^3R^4$ For example, the compound of formula (2) is reacted with from 1–10 molar equivalents, preferably about 2 molar equivalents, of phosgene in an inert organic solvent as defined above, preferably benzene The reaction takes place in the presence of from 1–5 molar equivalents, preferably about 2 molar equivalents of a tertiary organic base such as triethylamine or preferably pyridine. The reaction is conducted at from $0°–50°$ C., preferably about $25°$ C., for about 1–48 hours, preferably about 16 hours, and then filtered. To the filtrate is added from 1–5 molar equivalents, preferably about 2 molar equivalents of an organic base of the formula $HNR^3R^4$, and the mixture stirred at about $0°–50°$ C., preferably about $25°$ C., for about 1–12 hours, preferably about 2 hours. When the reaction is substantially complete, a compound of formula (7) where Z is —$C(O)NR^3R^4$ is isolated as above.

Step 8-Preparation of a comoound of Formula (II)

The reaction of Step 8 in its broadest aspect comprises the reaction of a compound of formula (7) with a reducing agent to give a compound of formula (II). Suitable reducing agents include, for example, lithium aluminum hydride, borane, triethyloxonium fluoroborate followed by sodium borohydride, sodium borohydride in the presence of a carboxylic acid, or preferably sodium borohydride in the presence of boron trifluoride etherate. Typically, a mixture is prepared of a compound of formula (7) and about 2 to 4 molar equivalents, preferably about 2.2 molar equivalents, of sodium borohydride in an ethereal solvent, for example diethyl ether, dimethoxyethane, dioxane, or preferably tetrahydrofuran. The mixture is cooled to about $0°$ to $20°$ C, preferably about $10°$ C., and about 2 to 6 molar equivalents, preferably about 3 molar equivalents, of boron trifluoride etherate is added. The mixture is then refluxed for about 15 minutes to 4 hours, preferably about 30 minutes. When the reaction is substantially complete, a (8aR,12aS,13aS)-12-substituted-5,6,8a,9,10,11,12,-12a,13,13a-decahydro-8H-isoquino[2,1g][1,6]naphthyridine derivative, a compound of formula (II), is separated conventionally in substantially pure form, and purified further if desired, for example by recrystallization of an acid salt.

The procedure most preferred for the preparation of compounds of formula (II) where Z is —$SO_2R$, in which R is as defined above, starts with the chiral acid salt of formula (IA) (obtained as shown in Reaction Scheme I) directly, rather than the free base of formula (I) as in Reaction Scheme III, thus eliminating the intervening step of conversion of the salt (IA) to the free base (I). This procedure is shown in more detail in Reaction Scheme V.

REACTION SCHEME V

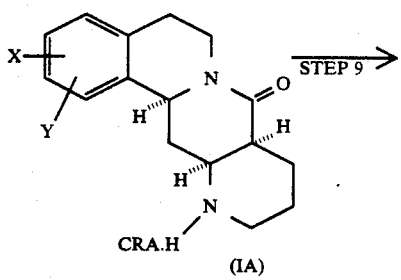

(IA)

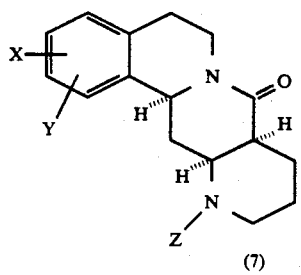

(7)

A compound of formula (IA) is mixed with an inert organic solvent, preferably dichloromethane, and about 2 to 10 molar equivalents, preferably about 3 molar equivalents, of a base, preferably a tertiary organic base (such as triethylamine, pyridine, N-methylpiperidine, N-methylmorpholine and the like, preferably N-methylmorpholine). The mixture is cooled to about 0° to 20° C., preferably about 10° C., and about 1-4 molar equivalents, preferably about 1.5 molar equivalents, of an appropriately substituted sulfonyl halide of formula $VSO_2R$ added and the mixture stirred for about 1-5 hours, preferably about 2 hours, at a temperature of about 0° to 40° C., preferably about 10°-16° C. When the reaction is substantially complete, a (8aS,12aS,13aS)-12-(substituted-sulfonyl)-5,6,8a,9,10,11,12,-12a,13,13a-decahydroisoquino[2,1-g][1,6]naphthyridin-8-one derivative, a compound of formula (7) where Z is $-SO_2R$, is isolated by conventional means, and purified, if desired, by crystallization from an inert solvent.

The compound of formula (7) is then converted to the compound of formula (II) as shown above.

Similarly, compounds of formula (I) and (IA) may be reacted to afford 12-substituted lactams analogous to those represented by the compound of formula (7) above (i.e. lactams substituted at the 12-position by other than Z as defined above), which may be similarly reduced to the corresponding 12-substituted decahydro-8H-isoquino-2,1-g][1,6]naphthyridine derivatives.

PREPARATIONS AND EXAMPLES

The following preparations and examples illustrate the invention but are not intended to limit its scope.

PREPARATION 1

Preparation of 6-methoxy-3,4-dihydroisoquinoline and Related Compounds of Formula (2)

A. A solution of 25 Kg of 3-methoxyphenethylamine, 9 Kg of toluene and 23 Kg of ethyl formate was heated to reflux (62°-76° C.) for 6 hours. The volatile components were removed under vacuum, the residue treated with a further 9 Kg of toluene and the solvent removed under vacuum, leaving 29.6 Kg of N-formyl-3-methoxy-phenethylamine as a pale yellow oil.

B. A solution of 29.4 Kg of N-formyl-3-methoxyphenethylamine in 30 litres of dichloromethane was added over 90 minutes to a well-stirred slurry of 38.4 Kg of phosphorus pentachloride in 30 litres of dichloromethane. An exothermic reaction ensued, causing the solvent to reflux at 35°-38° C. After addition was complete, the reaction mixture was hydrolysed by the addition of a mixture of 90 Kg of ice and 30 litres of hexane. After cooling the aqueous layer was separated, made basic with 144 Kg of 45% potassium hydroxide and extracted twice with 50 Kg of dichloromethane. After drying the organic layer with sodium sulfate the solvent was removed under reduced pressure to give 23 Kg of 6-methoxy-3,4-dihydroisoquinoline as an oil.

C. Similarly, replacing 3-methoxyphenethylamine with 3,4-methylenedioxyphenethylamine and following the procedures of Preparation 1A and 1B above, the following compound of formula (2) was made: 6,7-methylenedioxy-3,4-dihydroisoquinoline.

D. Similarly, replacing 3-methoxyphenethylamine with:

3,4-dimethoxyphenethylamine;
2,5-dimethoxyphenethylamine;
3,4-(ethylene-1,2-dioxy)phenethylamine;
2-methylphenethylamine;
3-methylphenethylamine;
4-methylphenethylamine;
3-ethylphenethylamine;
3,4-dimethylphenethylamine;
3-isobutylphenethylamine;
3-n-hexylphenethylamine;
3-methoxy-4-methylphenethylamine;
2-methoxyphenethylamine;
4-methoxyphenethylamine;
5-methoxyphenethylamine;
3-ethoxyphenethylamine;
3-isopropoxyphenethylamine;
3-isobutoxyphenethylamine;
3-n-hexyloxyphenethylamine;
3-hydroxyphenethylamine;
3,4-dihydroxyphenethylamine;
3,4-diethoxyphenethylamine;
3,4-di-n-butoxyphenethylamine;
2,3-methylenedioxyphenethylamine;
3-chlorophenethylamine;
4-chlorophenethylamine;
3-fluorophenethylamine; and
4-fluorophenethylamine;

and following the procedures of Preparation 1A and 1B above, the following corresponding compounds of formula (2) are made:

6,7-dimethoxy-3,4-dihydroisoquinoline;
5,8-dimethoxy-3,4-dihydroisoquinoline;
6,7-(ethylene-I,2-dioxy)-3,4-dihydroisoquinoline;
5-methyl-3,4-dihydroisoquinoline;
6-methyl-3,4-dihydroisoquinoline;
7-methyl-3,4-dihydroisoquinoline;
6-ethyl-3,4-dihydroisoquinoline;
6,7-dimethyl-3,4-dihydroisoquinoline;
6-isobutyl-3,4-dihydroisoquinoline;
6-n-hexyl-3,4-dihydroisoquinoline;
6-methoxy-7-methyl-3,4-dihydroisoquinoline;
5-methoxy-3,4-dihydroisoquinoline;
7-methoxy-3,4-dihydroisoquinoline;
8-methoxy-3,4-dihydroisoquinoline;
6-ethoxy-3,4-dihydroisoquinoline;

6-isopropoxy-3,4-dihydroisoquinoline;
6-isobutoxy-3,4-dihydroisoquinoline;
6-n-hexyloxy-3,4-dihydroisoquinoline;
6-hydroxy-3,4-dihydroisoquinoline;
6,7-dihydroxy-3,4-dihydroisoquinoline;
6,7-diethoxy-3,4-dihydroisoquinoline;
6,7-di-n-butoxy-3,4-dihydroisoquinoline;
5,6-methylenedioxy-3,4-dihydroisoquinoline;
7-chloro-3,4-dihydroisoquinoline;
6-chloro-3,4-dihydroisoquinoline;
7-fluoro-3,4-dihydroisoquinoline; and
6-fluoro-3,4-dihydroisoquinoline.

EXAMPLE 1

Preparation of 2,4-dioxo-9-methoxy-1,2,3,4,6,7-hexahydro-11bH-benzo[a]quinolizine and Related Compounds of Formula (4)

A. Step 1: Preparation of Formula (3) where X is 6-methoxy and Y is hydrogen

A solution of 23 Kg of 6-methoxy-3,4-dihydroisoquinoline, a compound of formula (2), in 140 Kg of isopropanol was heated to 50°–55° C., and 24.6 Kg of dimethyl 1,3-acetonedicarboxylate added, forming a precipitate. The reaction mixture was cooled to 23° C., and the precipitate filtered off and washed with isopropanol, giving 1-(1,3-methoxycarbonyl-2-oxopropan-1-yl)-6-methoxy,-1,2,3,4-tetrahydroisoquinoline. A sample was crystallized from isopropanol, m.p. 116°–117° C.

B. Step 2: Preparation of Formula (4) where X is 9-methoxy and Y is hydrogen

The 1-(1,3-methoxycarbonyl-2-oxopropan-1-yl)-6-methoxy-1,2,3,4-tetrahydroisoquinoline obtained in Step 1 was then suspended in 180 Kg of water and 40 Kg of 50% aqueous sodium hydroxide added. The resulting solution was stirred for 24 hours and then acidified to a pH of less than 3, maintaining the temperature at 25°–45° C., using 51 Kg of 37% hydrochloric acid. Carbon dioxide was evolved, and a precipitate formed. The mixture was stirred at 45° C. for 6 hours, while maintaining the Ph at less than 3 by the addition of portions of 37% hydrochloric acid as necessary (2.8 Kg added). The precipitate was filtered off, washed with water and dried for 48 hours at 75° C, giving 27.3 Kg of 2,4-dioxo-9-methoxy-1,2,3,4,6,7-hexahydro-11bHbenzo[a]quinolizine, approximately 80% pure. A sample was crystallized from ethyl acetate, m.p. 153°–154° C.

C. Preparation of Formula (4) where X and Y are 9,10-methylenedioxy

Similarly, replacing 6-methoxy-3,4-dihydroisoquinoline with 6,7-methylenedioxy-3,4-dihydroisoquinoline, obtained, for example, as described in Preparation 1C, and following the procedures of Example 1A and 1B above, the following compound of formula (4) was made:

2,4-dioxo-9,10-methylenedioxy-1,2,3,4,6,7-hexahydro11bH-benzo[a]quinolizine, m.p. 158°–160° C.

D. Preparation of Formula (4), varying X and Y

Similarly, replacing 6-methoxy-3,4-dihydroisoquinoline with compounds of formula (2), obtained, for example, as described in Preparation 1D, and following the procedures of Example 1A and 1B above, the following corresponding compounds of formula (4) are made:

2,4-dioxo-9,10-dimethoxy-1,2,3,4,6,7-hexahydro-11bHbenzo[a]quinolizine;
2,4-dioxo-8,11-dimethoxy-1,2,3,4,6,7-hexahydro-11bHbenzo[a]quinolizine;
2,4-dioxo-9,10-(ethylene-1,2-dioxy)-1,2,3,4,6,7-hexahydro-11bH-benzo[a]quinolizine;
2,4-dioxo-8-methyl-1,2,3,4,6,7-hexahydro-11bHbenzo[a]quinolizine;
2,4-dioxo-9-methyl-1,2,3,4,6,7-hexahydro-11bHbenzo[a]quinolizine;
2,4-dioxo-10-methyl-1,2,3,4,6,7-hexahydro-11bHbenzo[a]quinolizine;
2,4-dioxo-9-ethyl-1,2,3,4,6,7-hexahydro-11bHbenzo[a]quinolizine;
2,4-dioxo-9,10-dimethyl-1,2,3,4,6,7-hexahydro-11bHbenzo[a]quinolizine;
2,4-dioxo-9-isobutyl-1,2,3,4,6,7-hexahydro-11bHbenzo[a]quinolizine;
2,4-dioxo-9-n-hexyl-1,2,3,4,6,7-hexahydro-11bHbenzo[a]quinolizine;
2,4-dioxo-9-methyl-10-methyl-1,2,3,4,6,7-hexahydro-11bH-benzo[a]quinolizine;
2,4-dioxo-8-methoxy-1,2,3,4,6,7-hexahydro-11bHbenzo[a]quinolizine;
2,4-dioxo-10-methoxy-1,2,3,4,6,7-hexahydro-11bHbenzo[a]quinolizine;
2,4-dioxo-11-methoxy-1,2,3,4,6,7-hexahydro-11bHbenzo[a]quinolizine;
2,4-dioxo-9-ethoxy-1,2,3,4,6,7-hexahydro-11bHbenzo[a]quinolizine;
2,4-dioxo-9-isopropoxy-1,2,3,4,6,7-hexahydro-11bHbenzo[a]quinolizine;
2,4-dioxo-9-isobutoxy-1,2,3,4,6,7-hexahydro-11bHbenzo[a]quinolizine;
2,4-dioxo-9-n-hexyloxy-1,2,3,4,6,7-hexahydro-11bHbenzo[a]quinolizine;
2,4-dioxo-9-hydroxy-1,2,3,4,6,7-hexahydro-11bHbenzo[a]quinolizine;
2,4-dioxo-9,10-dihydroxy-1,2,3,4,6,7-hexahydro-11bHbenzo[a]quinolizine;
2,4-dioxo-9,10-diethoxy-1,2,3,4,6,7-hexahydro-11bHbenzo[a]quinolizine;
2,4-dioxo-9,10-di-n-butoxy-1,2,3,4,6,7-hexahydro-11bH-benzo[a]quinolizine;
2,4-dioxo-8,9-methylenedioxy-1,2,3,4,6,7-hexahydro-11bH-benzo[a]quinolizine;
2,4-dioxo-10-chloro-1,2,3,4,6,7-hexahydro-11bHbenzo[a]quinolizine;
2,4-dioxo-9-chloro-1,2,3,4,6,7-hexahydro-11bHbenzo[a]quinolizine;
2,4-dioxo-10-fluoro-1,2,3,4,6,7-hexahydro-11bHbenzo[a]quinolizine; and
2,4-dioxo-9-fluoro-1,2,3,4,6,7-hexahydro-11bHbenzo[a]quinolizine.

EXAMPLE 2

Alternative Preparation of 2,4-dioxo-9-methoxy-1,2,3,4,6,7-hexahydro-11bH-benzo[a]quinolizine and Related Compounds of Formula (4)

A. Step 1: Preparation of Formula (3) where X is 6-methoxy and Y is hydrogen

A mixture of 23.9 Kg of 6-methoxy-3,4-dihydroisoquinoline, a compound of formula (2), and 180 Kg of water was stirred at 23° C., and 24.3 Kg of dimethyl 1,3-acetone-dicarboxylate added over 30 minutes. The reaction mixture was heated to 60° C. over 40 minutes, maintained at 60° C. for 10 minutes, then cooled to 15° C.

B. Step 2: Preparation of Formula (4) where X is 9-methoxy and Y is hydrogen

To the reaction product of Step 1, 50 Kg of 50% sodium hydroxide was added. After 20 minutes a solution resulted, which was stirred for 4 days. The solution was extracted with 30 Kg of methylene chloride, followed by 40 Kg of methylene chloride. The aqueous residue was acidified at 15°–20° C. with 68 Kg of 32% hydrochloric acid over 1 hour to a pH of less than 3, and then stirred at 45° C. for 18 hours. The precipitate was filtered off, washed with 40 Kg of water and dried at 65° C. to constant weight, giving 27.9 Kg of 2,4-dioxo-9-methoxy-1,2,3,4,6,7-hexahydro-11bHbenzo[a]quinolizine.

C. Preparation of Formula (4) where X and Y are 9,10-methylenedioxy

Similarly, replacing 6-methoxy-3,4-dihydroisoquinoline with 6,7-methylenedioxy-3,4-dihydroisoquinoline, obtained, for example, as described in Preparation 1C, and following the procedures of Example 2A and 2B above, the following compound of formula (4) was made:

2,4-dioxo-9,10-methylenedioxy-1,2,3,4,6,7-hexahydro-11bH-benzo[a]quinolizine.

D. Preparation of Formula (4), varying X and Y

Similarly, replacing 6-methoxy-3,4-dihydroisoquinoline with compounds of formula (2), obtained, for example, as described in Preparation 1D, and following the procedures of Example 2A and 2B above, the corresponding compounds of formula (4) as shown in Example 1 are made.

EXAMPLE 3

Preparation of (±)-3-methoxy-5,6,9,10,11,12,13,13a-octahydroisoquino[2,1-g][1,6]naphthyridin-8-one and Related Compounds of Formula (5)

A. Step 3: Preparation of Formula (5) where X is 3-methoxy and Y is hydrogen

A solution of 27.3 Kg of 2,4-dioxo-9-methoxy-1,2,3,4,6,7-hexahydro-11bH-benzo[a]quinolizine, 19.6 Kg of 3-bromopropylamine hydrobromide and 22.8 Kg of 2,6-lutidine in 70 litres of n-butanol was refluxed for 1 hour. Butanol and excess 2,6-lutidine were removed under reduced pressure, and the solid residue dissolved in 150 litres of methanol at reflux temperature. The temperature was maintained above 70° C. while 150 litres of water was added. The mixture was cooled to 10° C., the precipitate filtered off and washed with 1:1 aqueous methanol. This product was recrystallized from a mixture of 150 Kg of methanol and 175 Kg of water. Drying under vacuum at 80° C. for three days gave 17.9 Kg of (±)-3-methoxy-5,6,9,10,11,12,13,13a-octahydroisoquino[2,1-g][1,6]naphthyridin-8-one, m.p. 202°–205° C.

B. Preparation of Formula (5) where X and Y are 2,3-methylenedioxy

Similarly, replacing 2,4-dioxo-9-methoxy-1,2,3,4,6,7-hexahydro-11bH-benzo[a]quinolizine with 2,4-dioxo-9,10-methylenedioxy-1,2,3,4,6,7-hexahydro-11bH-benzo[a]-quinolizine, obtained, for example, as described in Example 1C or 2C, and following the procedures of Example 3A above, the following compound of formula (5) was made: (±)-2,3-methylenedioxy-5,6,9,10,11,12,13,13a-octahydroisoquino[2,1-g][1,6]naphthyridin-8-one, m.p. 174°–175° C.

Preparation of Formula (5), varying X and Y

Similarly, replacing 2,4-dioxo-9-methoxy-1,2,3,4,6,7-hexahydro-11bH-benzo[a]quinolizine with compounds of formula (4), obtained, for example, as described in example 1D or 2D, and following the procedures of Example 3A above, the following corresponding formula of formula (5) are made: (±)-5,6,9,10,11,12,13,13a-octahydroisoquino[2,1-g][1,6]naphthyridin-8-one; (±)-2,3-dimethoxy-5,6,9,10,11,12,13,13a-octahydroisoquino[2,1-g][1,6]naphthyridin-8-one; (±)-1,4-dimethoxy-5,6,9,10,11,12,13,13a-octahydroisoquino[2,1-g][1,6]naphthyridin-8-one; (±)-2,3-(ethylene-1,2-dioxy)-5,6,9,10,11,12,13,12a-octahydroisoquino[2,1-g][1,6]naphthyridin-8-one (±)-1-methyl-5,6,9,10,11,12,13,13a-octahydroisoquino[2,1-g][1,6]naphthyridin-8-one; (±)-2-methyl-5,6,9,10,11,12,13,13a-octahydroisoquino[2,1-g][1,6]naphthyridin-8-one; (±)-3-methyl-5,6,9,10,11,12,13,13a-octahydroisoquino[2,1-g][1,6]naphthyridin-8-one; (±)-2,3-dimethyl-5,6,9,10,11,12,13,13a-octahydroisoquino[2,1-g][1,6]naphthyridin-8-one; (±)-3-ethyl-5,6,9,10,11,12,13,13a-octahydroisoquino[2,1-g][1,6]naphthyridin-8-one; (±)-3-isobutyl-5,6,9,10,11,12,13,13a-octahydroisoquino[2,1-g][1,6]naphthyridin-8-one; (±)-3-n-hexyl-5,6,9,10,11,12,13,13a-octahydroisoquino[2,1-g][1,6]naphthyridin-8-one; (±)-1-methoxy-5,6,9,10,11,12,13,13a-octahydroisoquino[2,1-g][1,6]naphthyridin-8-one; (±)-2-methoxy-5,6,9,10,11,12,13,13a-octahydroisoquino[2,1-g][1,6]naphthyridin-8-one; (±)-4-methoxy-5,6,9,10,11,12,13,13a-octahydroisoquino[2,1-g][1,6]naphthyridin-8-one; (±)-3-ethoxy-5,6,9,10,11,12,13,13a-octahydroisoquino[2,1-g][1,6]naphthyridin-8-one; (±)-3-isobutoxy-5,6,9,10,11,12,13,13a-octahydroisoquino[2,1-g][1,6]naphthyridin-8-one; (±)-3-n-hexyloxy-5,6,9,10,11,12,13,13a-octahydroisoquino[2,1-g][1,6]naphthyridin-8-one; (±)-3-hydroxy-5,6,9,10,11,12,13,13a-octahydroisoquino[2,1-g][1,6]naphthyridin-8-one; (±)-2,3-dihydroxy-5,6,9,10,11,12,13,13a-octahydroisoquino[2,1-g][1,6]naphthyridin-8-one; (±)-1,2-dimethoxy-5,6,9,10,11,12,13,13a-octahydroisoquino[2,1-g][1,6]naphthyridin-8-one; (±)-1,4-dimethoxy-5,6,9,10,11,12,13,13a-octahydroisoquino[2,1-g][1,6]naphthyridin-8-one; (±)-3,4-dimethoxy-5,6,9,10,11,12,13,13a-octahydroisoquino[2,1-g][1,6]naphthyridin-8-one; (±)-2,3-diethoxy-5,6,9,10,11,12,13,13a-octahydroisoquino[2,1-g][1,6]naphthyridin-8-one; (±)-2,3-di-n-butoxy-5,6,9,10,11,12,13,13a-octahydroisoquino[2,1-g][1,6]naphthyridin-8-one; (±)-1,2-methylenedioxy-5,6,9,10,11,12,13,13a-octahydroisoquino[2,1-g][1,6]naphthyridin-8-one; (±)-2-chloro-5,6,9,10,11,12,13,13a-octahydroisoquino[2,1-g][1,6]naphthyridin-8-one; (±)-3-chloro-5,6,9,10,11,12,13,13a-octahydroisoquino[2,1-g][1,6]naphthyridin-8-one; (±)-4-chloro-5,6,9,10,11,12,13,13a-octahydroisoquino[2,1-g][1,6]naphthyridin-8-one; (±)-3-bromo-5,6,9,10,11,12,13,13a-octahydroisoquino[2,1-g][1,6]naphthyridin-8-one; (±)-3-fluoro-5,6,9,10,11,12,13,13a-octahydroisoquino[2,1-g][1,6]naphthyridin-8-one; and (±)-2-fluoro-5,6,9,10,11,12,13,13a-octahydroisoquino[2,1-g][1,6]naphthyridin-8-one.

EXAMPLE 4

Preparation of the d-10-camphorsulfonic acid salt of (8aS,12aS,13aS)-3-methoxy-5,6,8a,9,10,11,12,12a 13,13a-decahydroisoquino[2,1-g][1,6]naphthyridin-8-one and Related Compounds of Formula (IA)

A. Step 4: Preparation of Formula (6) where X is 3-methoxy and Y is hydrogen

A solution of 17.9 Kg of (±)-3-methoxy-5,6,9,10,11,12,13,13a-octahydroisoquino[2,1-g][1,6]naphthyridin-8-one in 125 litres of acetic acid and 0.9 Kg of 5% Rh-Al$_2$O$_3$ was hydrogenated at 3–5 psi for 7 days at 18°–23° C. The catalyst was removed by filtration and solvent removed from the filtrate under reduced pressure, and the residue azeotroped with toluene, leaving a mixture of (±)-3-methoxy-5,6,8aβ,9,10,11,12,12aβ,13,13aβ-decahydroisoquino[2,1-g]-[1,6]naphthyridin-8-one, a compound of formula (6a); (±)-3-methoxy-5,6,8aβ,9,10,11,12,12aα,13,13aα-decahydroisoquino[2,1-g][1,6]naphthyridin-8-one, a compound of formula (6b); and (±)-3-methoxy-5,6,8aβ,9,10,11,12,-12aβ,13,13aβ-decahydroisoquino[2,1-g][1,6]naphthyridin-8-one, a compound of formula (6c).

B. Step 5: Preparation of Formula (IA) where X is 3-methoxy and Y is hydrogen

The mixture of stereoisomers obtained in Step 4 was dissolved in 215 litres of acetone and 5.85 Kg of d-10-camphorsulfonic acid added. The solution was allowed to stand for 1 hour, and if crystallization had not commenced the solution was seeded with the desired product. The solution was allowed to crystallize for 24 hours at room temperature, then filtered to give 7.63 Kg of the d-10-camphorsulfonic acid salt of (8aS,12aS,13aS)-3-methoxy-5,6,8a,9,10,11,12,12a,13,13a-decahydroisoquino[2,1-g][1,6]naphthyridin-8-one, m.p. 277°–278° C. N.B. Crystallizing for a period of time greater than 24 hours (25–72 hours) may yield a purer product.

If desired the salt product may be further purified as follows:

A mixture of 2.4 Kg of the d-10-camphorsulfonic acid salt of (8aS,12aS,13aS)-3-methoxy-5,6,8a,9,10,11,12,-12a,-13,13a-decahydroisoquino[2,1-g][1,6]naphthyridin-8-one (IA) and 9.6 litres of isopropanol was refluxed for 2 hours, cooled to 20° C. and allowed to stand for 1 hour. The solid was filtered off, washed with 2.3 litres of isopropanol, twice with 2.3 litres of acetone and dried in air to give 2.3 Kg to the purified product, m.p. 277°–278° C.

Preparation of Formula (IA) where X and Y are 2.3-methylenedioxy

Similarly, replacing (±)-3-methoxy-5,6,9,10,11,12,13,13a-octahydroisoquino[2,1-g][1,6]naphthyridin-8one with (±)-2,3-methylenedioxy-5,6,9,10,11,12,13,13a-octahydroisoquino[2,1-g][1,6]naphthyridin-8-one, obtained, for example, as described in Example 3B, and following the procedures of Example 4A and 4B above, replacing acetone with dioxane, the d-10-camphorsulfonic acid salt of the following compound was made:

(8aS,12aS,13aS)-2,3-methylenedioxy-5,6,8a,9,10,11,12,12a,13,13a-decahydroisoquino[2,1-g][1,6]naphthyridin-8-one, m.p. 274°–276° C.

D. Preparation of Formula (IA), varying X and Y

Similarly, replacing (±)-3-methoxy-5,6,9,10,11,12,13,13a-octahydroisoquino[2,1-g][1,6]naphthyridin-8-one with compounds of formula (5), obtained, for example, as described in Example 3C, and following the procedures of Example 4A and 4B above, the following corresponding compounds of formula (IA) are made as the d-10-camphorsulfonic acid salt:

(8aS,12aS,13aS)-5,6,8a,9,10,11,12,12a,13,13a-decahydroisoquino[2,1-g][1,6]naphthyridin-8-one;

(8aS,12aS,13aS)-2,3-dimethoxy-5,6,8a,9,10,11,12,-12a,13,13a-decahydroisoquino[2,1-g][1,6]naphthyridin-8-one;

(8aS,12aS,13aS)-1,4-dimethoxy-5,6,8a,9,10,11,12,-12a,13,13a-decahydroisoquino[2,1-g][1,6]naphthyridin-8-one;

(8aS,12aS,13aS)-2,3-(ethylene-1,2-dioxy)-5,6,8a,9,10,11,12,12a,13,13a-decahydroisoquino[2,1-g][1,6]naphthyridin-8-one;

(8aS,12aS,13aS)-1-methyl-5,6,8a,9,10,11,12,12a,13,-13a-decahydroisoquino[2,1-g][1,6]naphthyridin-8-one;

(8aS,12aS,13aS)-2-methyl-5,6,8a,9,10,11,12,12a,13,-13a-decahydroisoquino[2,1-g][1,6]naphthyridin-8-one;

(8aS,12aS,13aS)-3-methyl-5,6,8a,9,10,11,12,12a,13,-13a-decahydroisoquino[2,1-g][1,6]naphthyridin-8-one;

(8aS,12aS,13aS)-2,3-dimethyl-5,6,8a,9,10,11,12,-12a,13,13a-decahydroisoquino[2,1-g][1,6]naphthyridin-8-one;

(8aS,12aS,13aS)-3-ethyl-5,6,8a,9,10,11,12,12a,13,13a-decahydroisoquino[2,1-g][1,6]naphthyridin-8-one;

(8aS,12aS,13aS)-3-isobutyl-5,6,8a,9,10,11,12,12a,13,-13a-decahydroisoquino[2,1-g][1,6]naphthyridin-8one;

(8aS,12aS,13aS)-3-n-hexyl-5,6,8a,9,10,11,12,12a,13,-13a-decahydroisoquino[2,1-g][1,6]naphthyridin-8-one;

(8aS,12aS,13aS)-1-methoxy-5,6,8a,9,10,11,12,12a,13,-13a-decahydroisoquino[2,1-g][1,6]naphthyridin-8-one;

(8aS,12aS,13aS)-2-methoxy-5,6,8a,9,10,11,12,12a,13,-13a-decahydroisoquino[2,1-g][1,6]naphthyridin-8-one;

(8aS,12aS,13aS)-4-methoxy-5,6,8a,9,10,11,12,12a,13,-13a-decahydroisoquino[2,1-g][1,6]naphthyridin-8-one;

(8aS,12aS,13aS)-3-methoxy-2-methyl-5,6,8a,9,10,11,12,12a,13,13a-decahydroisoquino[2,1-g][1,6]naphthyridin-8-one;

(8aS,12aS,13aS)-3-ethoxy-5,6,8a,9,10,11,12,12a,13,-13a-decahydroisoquino[2,1-g][1,6]naphthyridin-8-one;

(8aS,12aS,13aS)-3-isopropoxy-5,6,8a,9,10,11,12,-12a,13,13a-decahydroisoquino[2,1-g][1,6]naphthyridin-8-one;

(8aS,12aS,13aS)-3-isobutoxy-5,6,8a,9,10,11,12,-12a,13,13a-decahydroisoquino[2,1-g][1,6]naphthyridin-8-one;

(8aS,12aS,13aS)-3-n-hexyloxy-5,6,8a,9,10,11,12,-12a,13,13a-decahydroisoquino[2,1-g][1,6]naphthyridin-8-one;

(8aS,12aS,13aS)-3-hydroxy-5,6,8a,9,10,11,12,12a,13,-13a-decahydroisoquino[2,1-g][1,6]naphthyridin-8-one;

(8aS,12aS,13aS)-2,3-dihydroxy-5,6,8a,9,10,11,12,-12a,13,13a-decahydroisoquino[2,1-g][1,6]naphthyridin-8one;

(8aS,12aS,13aS)-1,2-dimethoxy-5,6,8a,9,10,11,12,-12a,13,13a-decahydroisoquino[2,1-g][1,6]naphthyridin-8-one;

(8aS,12aS,13aS)-1,4-dimethoxy-5,6,8a,9,10,11,12,-12a,13,13a-decahydroisoquino[2,1-g][1,6]naphthyridin-8-one;

(8aS,12aS,13aS)-3,4-dimethoxy-5,6,8a,9,10,11,12,-12a,13,13a-decahydroisoquino[2,1-g][1,6]naphthyridin-8-one;

(8aS,12aS,13aS)-2,3-diethoxy-5,6,8a,9,10,11,12,-12a,13,13a-decahydroisoquino[2,1-g][1,6]naphthyridin-8-one;

(8aS,12aS,13aS)-2,3-di-n-butoxy-5,6,8a,9,10,11,12,-12a13,13a-decahydroisoquino[2,1-g][1,6]naphthyridin-8-one;

(8aS,12aS,13aS)-1,2-methylenedioxy-5,6,8a,9,10,11,12,12a,13,13a-decahydroisoquino[2,1-g][1,6]naphthyridin-8-one;

(8aS,12aS,13aS)-2-chloro-5,6,8a,9,10,11,12,12a,13,-13a-decahydroisoquino[2,1-g][1,6]naphthyridin-8-one;

(8aS,12aS,13aS)-3-chloro-5,6,8a,9,10,11,12,12a,13,-13a-decahydroisoquino[2,1-g][1,6]naphthyridin-8-one;

(8aS,12aS,13aS)-4-chloro-5,6,8a,9,10,11,12,12a,13,-13a-decahydroisoquino[2,1-g][1,6]naphthyridin-8-one;

(8aS,12aS,13aS)-3-bromo-5,6,8a,9,10,11,12,12a,13,-13a-decahydroisoquino[2,1-g][1,6]naphthyridin-8-one;

(8aS,12aS,13aS)-3-fluoro-5,6,8a,9,10,11,12,12a,13,-13a-decahydroisoquino[2,1-g][1,6]naphthyridin-8-one; and (8aS,12aS,13aS)-2-fluoro-5,6,8a,9,10,11,12,12a,13,-13a-decahydroisoquino[2,1-g][1,6]naphthyridin-8-one.

EXAMPLE 5

Conversion of the d-10-camphorsulfonic acid salt of (8aS,12aS,13aS)-3-methoxy-5,6,8a,9,10,11,12,12a,13,-13a-decahydroisoquino[2,1g][1,6]naphthyridin-8-one of Formula (IA) to the compound of Formula (I)

A. Step 6: Preparation of Formula (I) where X is 3-methoxy and Y is hydrogen

A mixture of the d-10-camphorsulfonic acid salt of (8aS,12aS,13aS)-3-methoxy-5,6,8a,9,10,11,12,12a,13,-13a-decahydroisoquino[2,1-g][1,6]naphthyridin-8-one (IA) and methylene chloride was made basic with aqueous sodium hydroxide, the organic layer washed with water and dried over sodium sulfate. The solvent was removed under reduced pressure to give (8aS,12aS,-13aS)-3-methoxy-5,6,8a,9,10,11,12,12a,13,13a-decahydroisoquino[2,1-g][1,6]naphthyridin-8-one. $^1$H NMR (CDCl$_3$), $\delta$ 1.4–2.0 (m, 6H), 2.4 (m, 1H), 2.6 (m, 1H), 2.7–2.9 (m, 5H), 3.4 (q, 1H), 3.75 (s, 3H), 4.6 (q, 1H), 4.7 (q, 1H), 6.68 (s, 1H), 6.8 (d, 1H), 7.1 (d, 1H); $[\alpha]_D$ −73.4° (C=0.5, CHCl$_3$).

B. Preparation of Formula (I) where X and Y are 2,3-methylenedioxy

Similarly, replacing the d-10-camphorsulfonic acid salt of (8aS,12aS,13aS)-3-methoxy-5,6,8a,9,10,11,12,-12a,13,13a-decahydroisoquino[2,1-g][1,6]naphthyridin-8-one with the d-10-camphorsulfonic acid salt of (8aS,-12aS,13aS)-2,3-methylenedioxy-5,6,9,10,11,12,13,13a-octahydroisoquino[2,1-g][1,6]naphthyridin-8-one, obtained, for example, as described in Example 4B, and following the procedures of Example 5A above, the following compound was made:

(8aS,12aS,13aS)-2,3-methylenedioxy-5,6,8a,9,10,11,12,12a,13,13a-decahydroisoquino[2,1-g][1,6]naphthyridin-8-one. $^1$H NMR (CDCl$_3$), $\delta$ 1.4–2.0 (m, 6H), 2.4 (m, 1H), 2.6 (m, 1H), 2.7–2.9 (m, 5H), 3.4 (q, 1H), 4.6 (q, 1H), 4.7 (q, 1H), 5.9 (s, 2H), 6.6 (d, 2H); $[\alpha]_D$ −157.3° (C=0.8, CHCl$_3$).

C. Preparation of Formula (I), varying X and Y

Similarly, replacing the d-10-camphorsulfonic acid salt of (8aS,12aS,13aS)-3-methoxy-5,6,8a,9,10,11,12,-12a,13,13a-decahydroisoquino[2,1-g][1,6]naphthyridin-8-one with compounds of formula (IA), obtained, for example, as described in Example 4C, and following the procedures of Example 5A above, the corresponding compounds of formula (I) as a free base are made.

EXAMPLE 6

Preparation of (8aS,12aS,13aS)-3-methoxy-12-methanesulfonyl-5,6,8a,9,10,11,12,12a,13,13a-decahydro isoquino[2,1-g][1,6naphthyridin-8-one and Related Compounds of Formula (7) where Z is —SO$_2$R A. Step 7: Preparation of Formula (7) where X is 3-methoxy, Y is hydrogen and Z is —SO$_2$R, where R is methyl A mixture of 660 g of the d-10-camphorsulfonic acid salt of (8aS,12aS,13aS)-3-methoxy-5,6,8a,9,10,11,12,-12a,13,13a-decahydroisoquino[2,1-g][1,6]naphthyridin-8-one (IA) in 8 litres of methylene chloride and 404 g of N-methylmorpholine was cooled in an ice bath to 10° C. and 153 ml of methanesulfonyl chloride was added over 30 minutes, allowing the temperature to rise to 16° C. The mixture was stirred at 10°–16° C. for 90 minutes, then washed sequentially with water, 1N hydrochloric acid, and water. The organic layer was dried over sodium sulfate and the solvent removed under reduced pressure. The residue was crystallized from methanol to give (8aS,12aS,13aS)-3-methoxy-12-methanesulfonyl-5,6,8a,9,10,11,12,12a,13,13a-decahydroisoquino[2,1-g][1,6]naphthyridin-8-one, m.p. 138°–140° C.

B. Preparation of Formula (7) where X and Y are 2,3-methylenedioxy and Z is —SO$_2$R, where R is methyl Similarly, replacing the d-10-camphorsulfonic acid salt of (8aS,12aS,13aS)-3-methoxy-5,6,8a,9,10,11,12,-12a,13,13a-decahydroisoquino[2,1-g][1,6]naphthyridin-8-one, with the d-10-camphorsulfonic acid salt of (8aS,-12aS,13aS)-2,3-methylenedioxy-5,6,8a,9,10,11,12,-12a,13,13a-decahydroisoquino[2,1-g][1,6]naphthyridin-8-one, obtained, for example, as described in Example 5B, and following the procedure of Example 6A above, the following compound was made: (8aS,12aS,13aS)-2,3-methylenedioxy-12-methanesulfonyl-5,6,8a,9,10,11,12,12a,13,13a-decahydroisoquino[2,1-g][1,6]-naphthyridin-8-one, m.p. 262°–263° C.

C. Preparation of Formula (7), varying X, Y and R

Similarly, optionally replacing (8aS,12aS,13aS)-3-methoxy-5,6,8a,9,10,11,12,12a,13,13a-decahydroisoquino[2,1-g][1,6]naphthyridin-8-one with a compound of formula (I), obtained, for example, as described in Example 5C, and optionally replacing methanesulfonyl chloride with other sulfonyl halides of formula VSO$_2$R and following the procedure of Example 6A above, the corresponding compounds of formula (7) where Z is -SO$_2$R are made.

EXAMPLE 7

Alternative Preparation of (8aS,12aS,13aS)-3-methoxy-12-methanesulfonyl-5,6,8a,9,10,11,12,12a,13,13a-decahydro isoquino[2,1g][1,6-naphthyridin-8-one and Related Compounds of Formula (7) where Z is —SO$_2$R A. Preparation of Formula (7) where X is 3-methoxy, Y is hydrogen and Z is —SO$_2$R, where R is methyl A solution of 11 g of (8aS,12aS,13aS)-3-methoxy-5,6,8a,9,10,11,12,12a,13,13a-decahydroisoquino[2,1-g][1,6]naphthyridin-8-one (I), obtained as shown in Example 4, in 300 ml of methylene chloride and 10 ml of triethylamine was cooled in an ice bath and 5 ml of methanesulfonyl chloride was added. The mixture was stirred at room temperature for 30 minutes, diluted with 100 ml of hexane, and extracted with water. The organic layer was dried over sodium sulfate and the solvent removed under reduced pressure. The residue was crystallized from isopropanol, to give 11 g of (8aS,12aS,13aS)-3-methoxy-12-methanesulfonyl5,6-,8a,9,10,11,12,12a,13,13a-decahydroisoquino[2,1-g][1,6]naphthyridin-8-one, m.p. 138°-140° C.

B. Preparation of Formula (7) where X and Y are 2,3methylenedioxy and Z is —SO$_2$R, where R is methyl Similarly, replacing (8aS,12aS,13aS)-3-methoxy-5,6,8a,9,10,11,12,12a,13,13a-decahydroisoquino[2,1-g][1,6]naphthyridin-8-one with (8aS,12aS,13aS)-2,3-methylenedioxy5,6,8a,9,10,11,12,12a,13,13a-decahydroisoquino[2,1-g][1,6]naphthyridin-8-one, obtained, for example, as described in Example 5B, and following the procedure of Example 7A above, the following compound was made:

(8aS,12aS,13aS)-2,3-methylenedioxy-12-methanesulfonyl-5,6,8a,9,10,11,12,12a,13,13a-decahydroisoquino[2,1-g][1,6]-naphthyridin-8-one, m.p. 262°-263° C.

C. Preparation of Formula (7), varying X, Y and R

Similarly, optionally replacing (8aS,12aS,13aS)-3-methoxy-5,6,8a,9,10,11,12,12a,13,13a-decahydroisoquino[2,1-g][1,6]naphthyridin-8-one with a compound of formula (I), obtained, for example, as described in Example 5C, and optionally replacing methanesulfonyl chloride with other sulfonyl halides of formula VSO$_2$R and following the procedure of Example 7A above, the corresponding compounds of formula (7) where Z is —SO$_2$R are made.

EXAMPLE 8

Preparation of (8aS,12aS,13aS)-12-N,N-Dimethylaminocarbonyl-5,6,8a,9,10,11,12,12a,13,13a-decahydroisoquino[2,1-g][1,6]naphthyridin-8-one and Related Compounds of Formula (7) where Z is —C(O)NR$^3$R$^4$ A. Preparation of Formula (7) where X and Y are hydrogen and Z is —C(O)NR$^3$R$^4$, where R$^3$ and R$^4$ are both methyl A solution of 4.5 g of (8aS,12aS,13aS)-5,6,8a,9,10,11,12,12a,13,13a-decahydroisoquino[2,1-g][1,6]naphthyridin-8-one, a compound of formula (I), and 6.6 ml of triethylamine in 100 ml of methylene chloride is stirred at room temperature and 1.56 ml of dimethylcarbamyl chloride is added. The mixture is stirred at room temperature for 16 hours, then solvent removed under reduced pressure. The residue is partitioned between 200 ml of methylene chloride and 50 ml of 2N sodium carbonate. The organic phase is dried over anhydrous magnesium sulfate, the solvent removed under reduced pressure, and the residue chromatographed on silica gel, eluting with 3% methanol/methylene chloride, to give (8aS,12aS,13aS)-12-N,N-dimethylaminocarbonyl5,6,8a,9,10,11,12,12a,13,13a-decahydroisoquino[2,1-g][1,6]naphthyridin-8-one.

B. Preparation of Formula (7), varying X, Y, R$^3$ and R$^4$

Similarly, optionally replacing (8aS,12aS,13aS) 5,6,8a,9,10,11,12,12a,13,13a-decahydroisoquino[2,1-g][1,6]naphthyridin-8-one with a compound of formula (I), obtained, for example, as described in Example 5C, and optionally replacing dimethylcarbamyl chloride with a carbamyl chloride of formula R$^3$R$^4$C(O)Cl, where R$^3$ and R$^4$ are as defined supra but are not hydrogen, and following the procedure in Example 8A above, the corresponding compounds of formula (7) where Z is —C(O)NR$^3$R$^4$ are made.

EXAMPLE 9

Preparation of (8aS,12aS,13aS)-3-methoxy-12-(R)-(+)-1phenylethylamino]carbonyl-5,6,8a,9,10,11,12,12a,13,13a-decahydroisoquino[2,1-g][1,6]naphthyridin-8-one and Related Compounds of Formula (7) where Z is —C(O)NHR$^4$ A. Preparation of Formula (7) where X is 3-methoxy, Y is hydrogen and Z is —C(O)NR$^3$R$^4$, where R$^3$ is hydrogen and R$^4$ is (R)—(+)-1-phenylethyl A solution of 1.95 g of (8aS,12aS,13aS)-3-methoxy-5,6,8a,9,10,11,12,12a,13,13a-decahydroisoquino[2,1-g][1,6]naphthyridin-8-one a compound of formula (I), and 1.0 g of (R)-(+)-α-methylbenzyl isocyanate in 50 ml of methylene chloride was stirred at room temperature for 30 minutes. Solvent was then removed under reduced pressure, and the residue chromatographed on silica gel, using multiple medium pressure chromatography and eluting with 5% methanol in ethyl acetate. The first compound eluted was (8aS,12aS,13aS)-3-methoxy-12-[(R)-(+)-1-phenylethylamino]carbonyl-5,6,8a,9,10,11,12,12a,13,13a-decahydroisoquino[2,1-g][1,6]naphthyridin-8-one, mp 198°-199° C., [α]D= +36.5 (CHCl$_3$).

B. Preparation of Formula (7) where Z is —C(O)NR$^3$R$^4$, in which R$^3$ is hydrogen, varying X, Y and R$^4$ Similarly, replacing (8aS,12aS,13aS)-3-methoxy-5,6,8a,9,10,11,12,12a,13,13a-decahydroisoquino[2,1-g][1,6]naphthyridin-8-one with a compound of formula (I), obtained, for example, as described in Example 5C, and following the procedure of Example 9A above, the corresponding compounds of formula (7) were prepared: (8aS,12aS,13aS)-12-[(R)-(+)-1-phenylethylamino]carbonyl-5,6,8a,9,10,11,12,12a,13,13a-decahydroisoquino[2,1-g][1,6]naphthyridin-8-one; and (8aS,12aS,13aS)-2,3-methylenedioxy-12-[(R)-(+)-1-phenylethylamino]carbonyl-5,6,8a,9,10,11, 12,12a,13,-13a-decahydroisoquino[2,1-g][1,6]naphthyridin-8-one.

C. Preparation of Formula (7) where Z is —C(O)NR$^3$R$^4$, in which R$^3$ is hydrogen, varying X, Y and R$^4$ Similarly, optionally replacing (8aS,12aS,13aS)-3-methoxy-5,6,8a,9,10,11,12,12a,13,13a-decahydroisoquino[2,1-g][1,6]naphthyridin-8-one with a compound of formula (I), obtained, for example, as described in Example 5C, and optionally replacing (R)-(+)-a-methylbenzyl isocyanate with an appropriate compound of formula R$^4$NCO and following the procedure of Example 7A above, the corresponding compounds of formula (7) where Z is —C(O)NHR$^4$ are prepared.

EXAMPLE 10

Preparation of (8aR,12aS,13aS1-3-methoxy-12-methanesulfonyl-5,6,8a,9,10,11,12,12a,13,13 a-decahydro-8H-isoquino[2,1-g][1,6]naphthyridine hydrochloride and Related Compounds of Formula (II)

A. Preparation of Formula (II) where X is 3-methoxy, Y is hydrogen and Z is —SO$_2$R, where R is methyl A slurry of 4.894 Kg of (8aS,12aS,13aS)-3-methoxy-12-methanesulfonyl-5,6,8a,9,10,11,12,12a, 13,13a- decahydroisoquino[2,1-g][1,6]naphthyridin-8-one (7) in 60 Kg of tetrahydrofuran was stirred with 1.103 Kg of sodium borohydride at about 10° C. This mixture was maintained at 10° C. while 5.836 Kg of boron trifluoride etherate was added. Upon completion of the addition the reaction mixture was refluxed for 30 minutes, cooled to 20° C., and 67 litres of 1N hydrochloric acid added cautiously. The majority of the solvent was then removed by distillation at atmospheric pressure, the residue cooled to below 30° C. and aqueous 6N sodium hydroxide solution added until the pH reached 12.2 (about 35 litres). The reaction mixture was then extracted with methylene chloride, and the combined extracts washed with water. The solvent was removed by distillation at atmospheric pressure, replacing the methylene chloride with ethanol until the pot temperature reached 78° C. The solution was then cooled to about 70° C. and concentrated aqueous hydrochloric acid (1.3 litres) was added. The slurry was stirred at about 70° C. for 10 minutes, cooled to 20° C. and then stood for 12 hours The product was filtered, washed with 33 Kg of cold ethanol and dried under vacuum at 40°–45° C., giving (8aR,12aS,13aS)-3-methoxy-12-methanesulfonyl-5,6,8a,9,10,11,12,12a,13,13a-decahydro-8H-isoquino[2,1-g][1,6]naphthyridine hydrochloride, m.p. 257°–258° C.

B. Preparation of Formula (II) where X and Y are 2,3-methylenedioxy and Z is —SO$_2$R, where R is methyl Similarly, replacing (8aS,12aS,13aS)-3-methoxy-12-methanesulfonyl-5,6,8a,9,10,11,12,12a,13,13a-decahydroisoquino[2,1-g][1,6]naphthyridin-8-one with 8aS,12aS,13aS)-2,3-methylenedioxy-12-methanesulfonyl-5,6,8a,9,10,11,12,12a,13,13a-decahydroisoquino[2,1-g][1,6]naphthyridin-8-one, obtained, for example, as described in Example 6B or 7B, and following the procedure of Example 10A above, the following compound was made:

(8aR,12aS,13aS)-2,3-methylenedioxy-12-methanesulfonyl-5,6,8a,9,10,11,12,12a,13,13a-decahydro-8H-isoquino[2,1g][1,6]naphthyridine hydrochloride, mp 263°–265° C.

C. Preparation of Formula (II), varying X, Y and R

Similarly, optionally replacing (8aS,12aS,13aS)-3-methoxy-12-methanesulfonyl-5,6,8a,9,10,11,12,12a,13,-13a-decahydroisoquino[2,1-g][1,6]naphthyridin-8-one with a compound of formula (7), obtained, for example, as described in Example 6C or 7C, and following the procedure of Example 10A above, the corresponding compounds of formula (II) are made as the hydrochloride salt.

EXAMPLE 11

Preparation of (8aR,12aS,13aS)-3-methoxy-12-[(R)-(+)-phenylethylamino[carbonyl-5,6,8a,9,10,11,12,12a,13,13a-decahydro-8H-isoquino[2,1-g][1,6]naphthyridine and Related Compounds of Formula (II)

A. Preparation of Formula (II) where X is 3-methoxy, Y is hydrogen and Z is —C(O)NR$^3$R$^4$, where R$^3$ is hydrogen and R$^4$ is (R)-(+)-1-phenylethyl A solution of 11.5 g of (8aS,12aS,13aS)-3-methoxy-12-(R)-(+)-1-phenylethylamino]carbonyl-[(R)-(+)-1-phenylethylamino]carbonyl-5,6,8a,9,10,11,12,12a,13,-13a-decahydroisoquino[2,1-g][1,6]naphthyridin-8-one (7), in 50 ml of tetrahydrofuran was added slowly to a solution of 2.0 g of lithium aluminum hydride in 75 ml of tetrahydrofuran. The resulting mixture was stirred at reflux for 2 hours, cooled, and treated sequentially with 2.5 ml of water, 2.5 ml of 15% sodium hydroxide, and 7.5 ml of water. The mixture was filtered and the filtrate was evaporated to afford 8.8 g of (8aR,12aS,13aS)-3-methoxy-12-[(R)-(+)-1-phenylethylamino]carbonyl-5,6,8a,9,10,11,12,12a,13,13a-decahydro-8H-isoquino[2,1-g][1,6]naphthyridine.

B. Preparation of Formula (II) where Z is —C(O)NR$^3$R$^4$, in which R$^3$ is hydrogen, varying X, Y and R$^4$ Similarly, replacing (8aS,12aS,13aS)-3-methoxy-12-[(R)-(+)-1-phenylethylamino]carbonyl-5,6,8a,9,10,11,12,12a,13,13a-decahydroisoquino[2,1-g][1,6]naphthyridin-8-one with other compounds of formula (7), obtained, for example, as described in Example 9C, and following the procedure of Example 11A above, the following compounds of formula (II) were prepared:

(8aR,12aS,13aS)-12-[(R)-(+)-1-phenylethylamino]-carbonyl-5,6,8a,9,10,11,12,12a,13,13a-decahydro-8H-isoquino[2,1-g][1,6]naphthyridine; and (8aR,12aS,13aS)-2,3-methylenedioxy-12-[(R)-(+)-1-phenylethylamine]carbonyl-5,6,8a,9,10,11,12,12a,13,-13a-decahydro-8H-isoquino[2,1-g][1,6]naphthyridine.

Preparation of Formula (II) where Z is —C(O)NR$^3$R$^4$, in which R$^3$ is hydrogen, varying X, Y and R$^4$ Similarly, replacing (8aS,12aS,13aS) 3-methoxy-12-[(R)-(+)-1-phenylethylamino]carbonyl-5,6,8a,9,10,11,12,12a,13,13a-decahydroisoquino[2,1-g][1,6]naphthyridin-8-one with a compound of formula (7), obtained, for example, as described in Example 9C, and following the procedure of Example 11A above, other compounds of formula (II) are prepared.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process step or steps, to the objective, spirit and scope of the present invention. All such modifications are intended to be within the scope of the claims appended hereto.

What is claimed is:

1. A process for the preparation of single enantiomers represented by the formula:

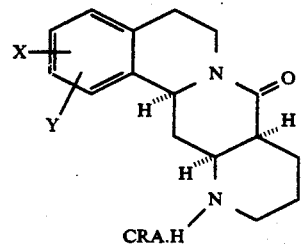

wherein:
X and Y are independently hydrogen; lower alkyl of one to six carbon atoms; lower alkoxy of one to six carbon atoms; or halo; or X and Y when adjacent and taken together are methylenedioxy or ethylene-1,2-dioxy; and
CRA is a chiral resolving acid;
which process comprises:

(a) dissolving a mixture of stereoisomers, including said single enantiomer, represented by the formula:

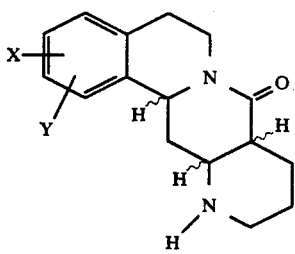

wherein each wavy line independently represents a bond in either the α or β position; together with a chiral resolving acid in a suitable solvent; and;
(b) allowing the solution to crystallize.

2. The process of claim 1, wherein said mixture of stereoisomers comprises a mixture of said single enantiomer as a racemic compound admixed with at least one other racemic compound represented by the formulae:

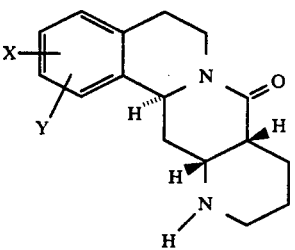

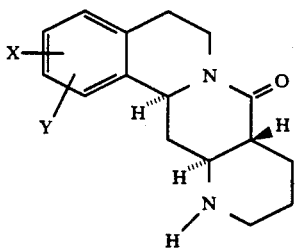

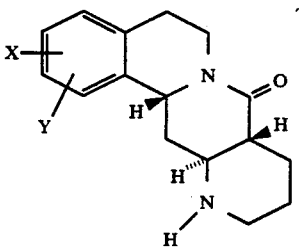

wherein X and Y are as defined above.

3. The process of claim 2, wherein said mixture of stereoisomers comprises a mixture of said single enantiomer as a racemic compound admixed with both racemic compounds represented by the formulae

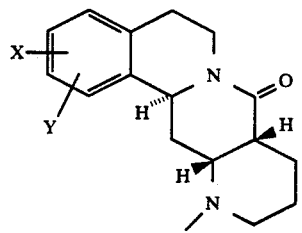

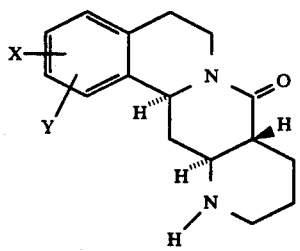

wherein X and Y are as defined above

4. The process of claim 1, wherein the said chiral resolving acid is d-10-camphorsulfonic acid.

5. The process of claim 4, wherein said solvent is chosen from dioxane and a di(lower alkyl)ketone, or a combination thereof.

6. The process of claim 5, wherein the molar ratio of said d-10-camphorsulfonic acid to said single enantiomer is between about 0.9 to 1 and 1.1 to 1.

7. The process of claim 6, wherein the solution is allowed to crystallize at a temperature of about 20°-25° C.

8. The process of claim 7, wherein said ratio is 1.0 and the solvent is acetone.

9. The process of claim 8, wherein X is 3-methoxy and Y is hydrogen.

10. The process of claim 7, wherein said ratio is 1.0 and the solvent is dioxane.

11. The process of claim 10, wherein X and Y taken together is 2,3-methylenedioxy.

12. The process of claim 1, comprising the further steps of:
(c) contacting the single enantiomer so-prepared with a compound of the formula ZV, wherein:
V is chloro or bromo; and
Z is —SO$_2$R or —C(O)NR$^3$R$^4$, wherein:
R is lower alkyl of one to six carbon atoms; phenyl optionally substituted by one or two substituents chosen from halo, amino, lower alkyl of one to four carbon atoms and lower alkoxy groups of one to four Carbon atoms; —(CH$_2$)$_m$OR$^1$; or —NR$^1$R$^2$; wherein:
m is an integer of 1 to 6 and R$^1$ and R$^2$ are independently lower alkyl; or R$^1$ and R$^2$ taken together with the nitrogen to which they are attached represent a heterocycle of the formula:

wherein A is —CH$_2$—, —NR$^1$—or oxygen; and

R³ and R⁴ are independently alkyl of 1–8 carbon atoms; phenyl; or phenyl lower alkyl; in which any phenyl group may be optionally substituted by one or two substituents chosen from halo, lower alkyl of one to four carbon atoms and lower alkoxy of one to four carbon atoms;
to give a compound of the formula:

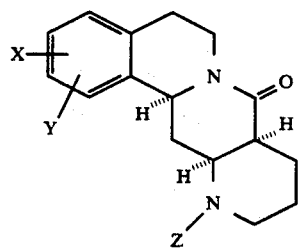

followed by:
(d) contacting said product with a reducing agent chosen from the group consisting of lithium aluminum hydride, borane, triethyloxonium fluoroborate followed by sodium borohydride, sodium borohydride in the presence of a carboxylic acid, and sodium borohydride in the presence of boron trifluoride etherate, to give a compound represented by the formula:

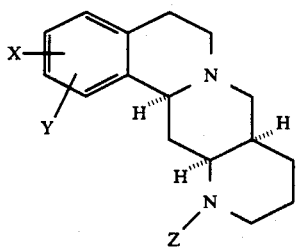

in which:
X, Y and Z are as defined above.

13. The process of claim 12, wherein the reaction of step (c) is carried out in the presence of a base chosen from triethylamine, pyridine, N-methylpiperidine and N-methylmorpholine, and said reducing agent is sodium borohydride in the presence of boron trifluoride etherate, in tetrahydrofuran as a solvent.

14. The process of claim 1, comprising the further step of:
(e) contacting the single enantiomer so-prepared with a base to give a single enantiomer represented by the formula:

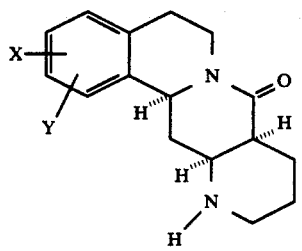

wherein X and Y are as defined above.

15. The process of claim 14, comprising the further steps of:
(f) contacting the single enantiomer so-prepared with a compound of the formula ZV, wherein:
V is chloro or bromo; and
Z is —SO₂R or —C(O)NR³R⁴, in which;
R is lower alkyl of one to six carbon atoms; phenyl optionally substituted by one or two substituents chosen from halo, amino, lower alkyl of one to four carbon atoms and lower alkoxy groups of one to four carbon atoms; —(CH₂)ₘOR¹; or —NR¹R²; wherein:
m is an integer of 1 to 6 and R¹ and R² are independently lower alkyl; or R¹ and R² taken together with the nitrogen to which they are attached represent a heterocycle of the formula:

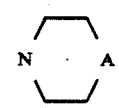

wherein A is —CH₂—, —NR¹— or oxygen; and
R³ and R⁴ are independently alkyl of 1–8 carbon atoms; phenyl; or phenyl lower alkyl; in which any phenyl group may be optionally substituted by one or two substituents chosen from halo, lower alkyl of one to four carbon atoms and lower alkoxy of one to four carbon atoms;
to give a compound of the formula:

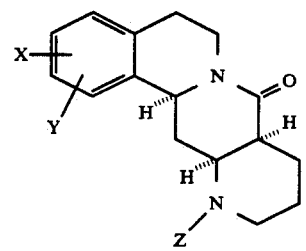

followed by:
(g) contacting said product with a reducing agent chosen from the group consisting of lithium aluminum hydride, borane, triethyloxonium fluoroborate followed by sodium borohydride, sodium borohydride in the presence of a carboxylic acid and sodium borohydride in the presence of boron trifluoride etherate, to give a compound represented by the formula:

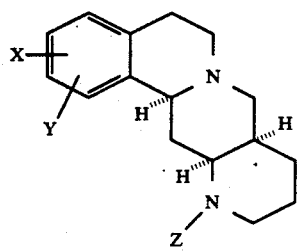

in which:
X, Y and Z are as defined above.

16. The process of claim 15, wherein the reaction of step (f) is carried out in the presence of a base chosen from triethylamine, pyridine, N-methylpiperidine and N-methylmorpholine, and said reducing agent is sodium borohydride in the presence of boron trifluoride etherate, in tetrahydrofuran as a solvent.

17. The process of claim 1, wherein said mixture of said stereoisomers represented by the formula

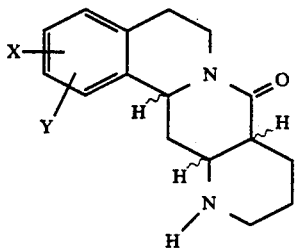

is obtained by hydrogenating a compound of the formula:

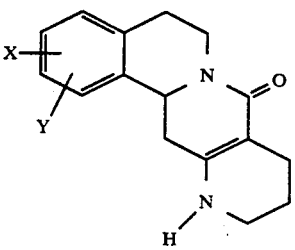

in a solvent chosen from the group consisting of ethanol, n-propanol, isopropanol and acetic acid, in the presence of a catalyst chosen from the group consisting of palladium on carbon, platinum oxide, rhodium on carbon, rhodium on alumina and platinum on alumina.

18. The process of claim 17, wherein said hydrogenation is carried out at a pressure of about 2–5 pounds per square inch, the catalyst is rhodium on alumina or platinum on alumina and the solvent is acetic acid.

19. The process of claim 18, wherein X is 3-methoxy and Y is hydrogen or X and Y taken together is 2,3-methylenedioxy.

20. The process of claim 17, wherein the compound of the formula:

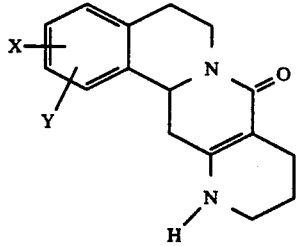

is obtained by contacting a compound of the formula

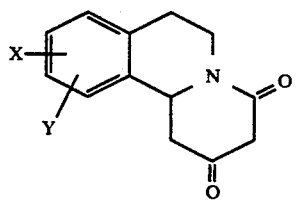

with a compound of the formula $W(CH_2)_3NH_2,HW$, wherein W is chloro or bromo, in a solvent chosen from the group consisting of ethanol, n-propanol, isopropanol and n-butanol, in the presence of a base, at a temperature between 80° C. and the reflux temperature of the said solvent.

21. The process of claim 20, wherein said compound of the formula $W(CH_2)_3NH_2.HW$ is 3-bromopropylamine hydrobromide, said solvent is n-butanol at reflux temperature and said base is 2,6-lutidine 22. The process of claim 21, wherein X is 3-methoxy and Y is hydrogen or X and Y taken together is 2,3-methylenedioxy.

* * * * *